0

(12) United States Patent
Gregori et al.

(10) Patent No.: US 9,234,174 B2
(45) Date of Patent: Jan. 12, 2016

(54) TOLEROGENIC DENDRITIC CELLS, METHOD FOR THEIR PRODUCTION AND USES THEROF

(75) Inventors: Silvia Adriana Gregori, Milan (IT); Maria Grazia Roncarolo, Milan (IT); Rosa Bacchetta, Milan (IT)

(73) Assignees: OSPEDALE SAN RAFFAELE S.R.L., Milan (IT); FONDAZIONE TELETHON, Rome (IT)

( * ) Notice: Subject to any disclaimer, the term of this patent is extended or adjusted under 35 U.S.C. 154(b) by 1005 days.

(21) Appl. No.: 12/300,764

(22) PCT Filed: Mar. 30, 2007

(86) PCT No.: PCT/EP2007/002896
§ 371 (c)(1),
(2), (4) Date: Nov. 13, 2008

(87) PCT Pub. No.: WO2007/131575
PCT Pub. Date: Nov. 22, 2007

(65) Prior Publication Data
US 2010/0041145 A1   Feb. 18, 2010

Related U.S. Application Data

(60) Provisional application No. 60/799,975, filed on May 12, 2006.

(51) Int. Cl.
*C12N 5/0784* (2010.01)
*C12N 5/0783* (2010.01)
*C12N 5/00* (2006.01)
*C12N 5/02* (2006.01)
*C12N 5/07* (2010.01)
*A61K 35/12* (2015.01)

(52) U.S. Cl.
CPC .............. *C12N 5/0636* (2013.01); *C12N 5/064* (2013.01); *A61K 2035/122* (2013.01); *A61K 2035/124* (2013.01); *C12N 2501/22* (2013.01); *C12N 2501/23* (2013.01); *C12N 2501/231* (2013.01)

(58) Field of Classification Search
None
See application file for complete search history.

(56) References Cited

U.S. PATENT DOCUMENTS

| 6,010,905 | A  | * | 1/2000 | Cohen et al. | 435/372 |
| 6,277,635 | B1 | * | 8/2001 | Roncarolo et al. | 435/372.3 |
| 2003/0211100 | A1 | * | 11/2003 | Bedian et al. | 424/144.1 |
| 2004/0241167 | A1 | * | 12/2004 | Suciu-Foca et al. | 424/152.1 |
| 2007/0269436 | A1 | * | 11/2007 | Chen | 424/139.1 |

FOREIGN PATENT DOCUMENTS

| WO | 03/102162 A2 | 12/2003 |
| WO | 03/102162 A3 | 12/2003 |
| WO | 2004/087899 A1 | 10/2004 |

OTHER PUBLICATIONS

Min et al "Antigen-Induced, Tolerogenic CD11c+,CD11b+ Dendritic Cells Are Abundant in Peyer's Patches During the Induction of Oral Tolerance to Type II Collagen and Suppress Experimental Collagen-Induced Arthritis" (Arthritis & Rheumatism, vol. 54, No. 3, Mar. 2006, pp. 887-898).*
Hauben et al in "IL-10-dependent Induction of a new subset of Tolerogenic Antigen Presenting Cells" (Faseb Journal Meeting Abstract, abstract only, published Apr. 2004).*
Behi et al in "New insights into cell responses involved in experimental autoimmune encephalomyelitis and multiple sclerosis" (Immunology Letters 2005 vol. 96, published Sep. 1, 2004, pp. 11-26).*
Groux et al ('04) in "Role of dendritic cells in the generation of regulatory T cells" (Seminars in Immunology vol. 16, available online 2004, pp. 99-106).*
Amiodo et al., "HLA-G expressing DC-10 and CD4+ T cells accumulated in human decidua during pregnancy" 74 Human Immunology 406-411 (2013).*
Mitra et al., "Psoriatic Skin-Derived Dendritic Cell Function is Inhbited by Exogenous IL-10" 154(6) The Journal of Immunology 2668-2677 (1995).*
Wakkach et al., "Characterization of Dendritic Cells that Induce Tolerance and T Regulatory 1 Cell Differentiation In Vivo" 18 Immunity 605-617 (2003).*
Ramadan et al., "In vitro generation of human CD86+ dendritic cells from CD34+ haematopoietic progenitors by PMA and in serum-free medium" 125 Clinical and Experimental Immunology 237-244 (2001).*
Steinbrink, et al., "Induction of tolerance by IL-10-treated dendritic cells", Journal of Immunology, US. vol. 159, No. 10, Nov. 15, 1997, pp. 4772-4780, XP002265198.
Steinbrink, et al., "CD4+ and CD8+ anergic T cells induced by interleukin-10-treated human dendritic cells display antigen-specific suppressor activity," Blood. vol. 99, No. 7, Apr. 1, 2002, pp. 2468-2476, XP002445320.
Hauben, et al., "IL-10-dependent Induction of a new subset of Tolerogenic Antigen Presenting Cells", FASEB Journal, vol. 18, No. 4-5, 2004, pages Abst. 91.4, XP002445321, FASEB Meeting on Experimental Biology: Translating the Genome; Washington, DC, USA; Apr. 17-21, 2004.
Gregori, et al., "Induction of CD4+regulatory T cells by IL-10-modulated dendritic cells", Journal of Immunology, US, vol. 176, no. suppl, May 1, 2006, pp. 216, XP009087661.
Gregori, et al., "Differentiation of type 1 T regulatory cells (Tr1) by tolerogenic DC-10 requires the IL-10-dependent ILT4/HLA-G pathway", Blood, 12(116):935-944, 2010.

* cited by examiner

Primary Examiner — Nancy J Leith
(74) Attorney, Agent, or Firm — Lucas & Mercanti LLP

(57) ABSTRACT

The present invention relates to a tolerogenic dendritic cell population (Tr-DC) capable of generating a population of T cells having regulatory activity, method of production and uses thereof. Furthermore, soluble HLA-G promotes the differentiation of a population of T cells with regulatory activity.

15 Claims, 24 Drawing Sheets

Figure 1:
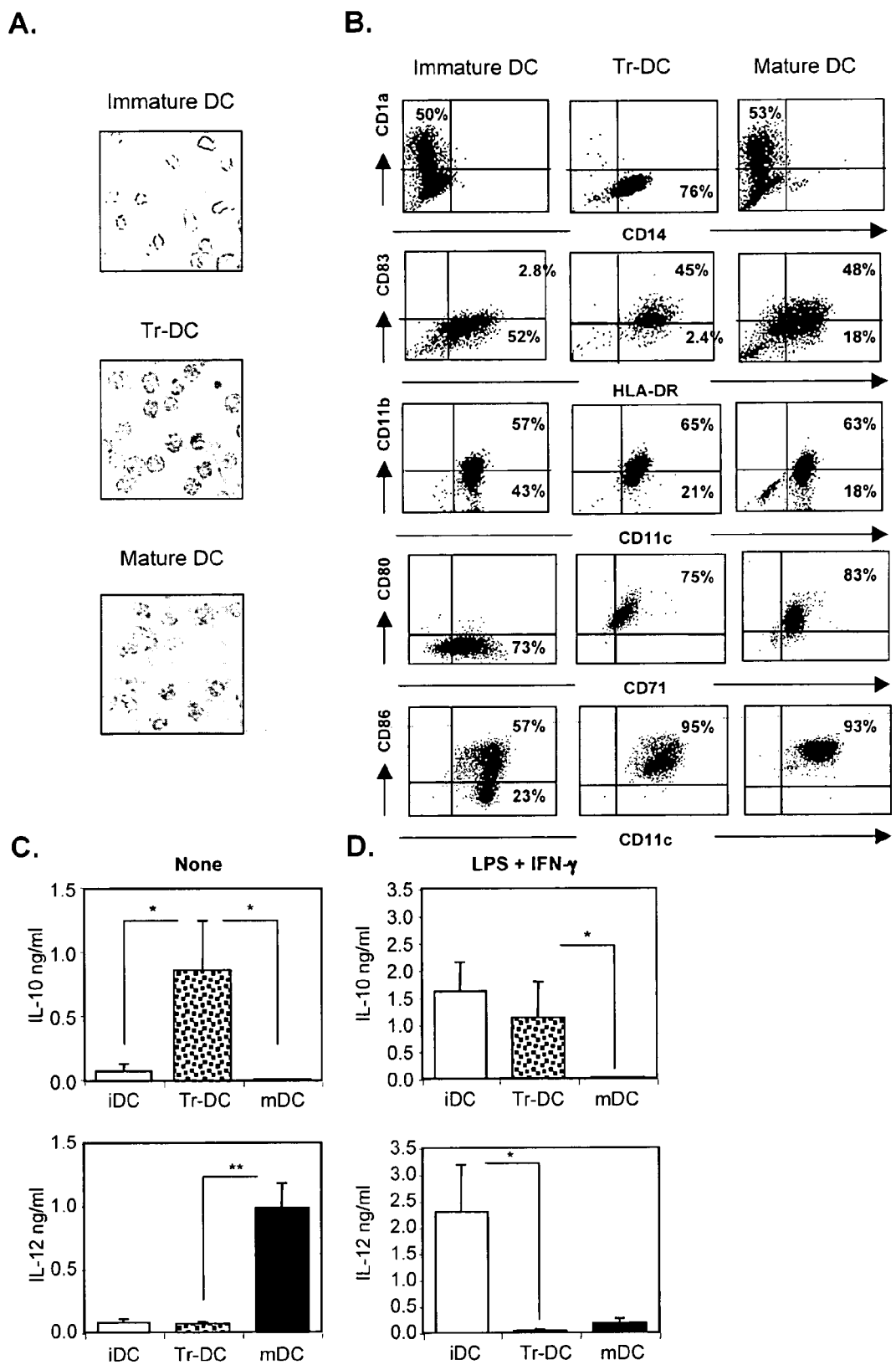

A.

B.

A

B

A.

B.

New tolerogenic DC

```
SEQUENCE LISTING

<160> NUMBER OF SEQ ID NOS: 1

<210> SEQ ID NO 1
<211> LENGTH: 319
<212> TYPE: PRT
<213> ORGANISM: Homo sapiens

<400> SEQUENCE: 1

Met Val Val Met Ala Pro Arg Thr Leu Phe Leu Leu Leu Ser Gly Ala
1               5                   10                  15

Leu Thr Leu Thr Glu Thr Trp Ala Gly Ser His Ser Met Arg Tyr Phe
            20                  25                  30

Ser Ala Ala Val Ser Arg Pro Gly Arg Gly Glu Pro Arg Phe Ile Ala
        35                  40                  45

Met Gly Tyr Val Asp Asp Thr Gln Phe Val Arg Phe Asp Ser Asp Ser
    50                  55                  60

Ala Cys Pro Arg Met Glu Pro Arg Ala Pro Trp Val Glu Gln Glu Gly
65                  70                  75                  80
```

-continued

```
Pro Glu Tyr Trp Glu Glu Thr Arg Asn Thr Lys Ala His Ala Gln
            85                  90              95

Thr Asp Arg Met Asn Leu Gln Thr Leu Arg Gly Tyr Tyr Asn Gln Ser
            100             105                 110

Glu Ala Ser Ser His Thr Leu Gln Trp Met Ile Gly Cys Asp Leu Gly
            115             120             125

Ser Asp Gly Arg Leu Leu Arg Gly Tyr Glu Gln Tyr Ala Tyr Asp Gly
    130             135                 140

Lys Asp Tyr Leu Ala Leu Asn Glu Asp Leu Arg Ser Trp Thr Ala Ala
145                 150                 155                 160

Asp Thr Ala Ala Gln Ile Ser Lys Arg Lys Cys Glu Ala Ala Asn Val
                165                 170                 175

Ala Glu Gln Arg Arg Ala Tyr Leu Glu Gly Thr Cys Val Glu Trp Leu
                180                 185                 190

His Arg Tyr Leu Glu Asn Gly Lys Glu Met Leu Gln Arg Ala Asp Pro
            195                 200                 205

Pro Lys Thr His Val Thr His His Pro Val Phe Asp Tyr Glu Ala Thr
    210                 215                 220

Leu Arg Cys Trp Ala Leu Gly Phe Tyr Pro Ala Glu Ile Ile Leu Thr
225                 230                 235                 240

Trp Gln Arg Asp Gly Glu Asp Gln Thr Gln Asp Val Glu Leu Val Glu
                245                 250                 255

Thr Arg Pro Ala Gly Asp Gly Thr Phe Gln Lys Trp Ala Ala Val Val
                260                 265                 270

Val Pro Ser Gly Glu Glu Gln Arg Tyr Thr Cys His Val Gln His Glu
            275                 280                 285

Gly Leu Pro Glu Pro Leu Met Leu Arg Trp Ser Lys Glu Gly Asp Gly
    290                 295                 300

Gly Ile Met Ser Val Arg Glu Ser Arg Ser Leu Ser Glu Asp Leu
305                 310                 315
```

TOLEROGENIC DENDRITIC CELLS, METHOD FOR THEIR PRODUCTION AND USES THEROF

BACKGROUND OF INVENTION

Hematopoietic stem cell (HSC) transplantation is increasingly used for the treatment of a number of malignant and non-malignant disorders of both hematopoietic and non-hematopoietic origin. However, rejection responses mediated by the immune system of the donor against the recipient, termed graft versus host disease (GvHD) remains a major cause of morbidity. Organ transplantation is the best available established technique for the treatment of end stage failure of most essential organs (liver, heart, and lungs), but allograft rejection mediated by the host is a major hurdle to long-term graft survival. A panel of immunosuppressive drugs is now available to prevent acute GvHD and allograft rejection including steroids, cyclosporin, metotrexate, cyclophosphamide, anti-thymocyte globulin, and anti-CD3 mAb. While these agents have significantly improved graft outcomes, their use have been associated with numerous and rather significant toxicities. Moreover, continuous drug administration leads to a sustained state of immunosuppression with consequent high risk of infections. All these effects are linked to the non-selective mode of action of the immunosuppressive drugs.

A valid alternative to immunosuppressive regimens for prevention of GvHD and of allograft rejection is the induction of tolerance to the alloantigens expressed by the recipient or the graft. This tolerance strategy should selectively target only a small fraction of potentially alloreactive T cells and leave the rest of the immune system intact.

In autoimmune diseases, undesired immune response to self-antigens lead to destruction of peripheral tissues. Treatments of autoimmune diseases are currently based on modulation of inflammation and non-specific immunosuppression. Similarly to the prevention of allograft rejection and GvHD, this approach is frequently not effective long-term due to the side effects of immunosuppression including infections and cancer, and high risk of disease relapse once the drug is withdrawn. An alternative strategy is based on the induction of specific immune tolerance with the ultimate goal to down-regulate the pathogenic immune response to self-antigens and to keep intact the mechanisms of host defence.

In chronic inflammatory diseases and in allergies an altered immune response to pathogenic and non-pathogenic antigens occurs. This may be due to an unbalance between effector and regulatory immune responses. Conventional anti-inflammatory or immunosuppressive therapies are insufficient to restore this balance. Moreover, the benefit of these therapies is not long-lasting after drugs withdrawn. The induction of antigen-specific tolerance mechanisms able to suppress undesired responses would represent a major advantage. Indeed, IL-10-producing T cells with regulatory properties, which are specific for different non-pathogenic antigens have been isolated in healthy donors.

In addition to central tolerance which occurs during T-cell ontogeny in the thymus and is mediated by clonal deletion of self-reactive T cells, peripheral T-cell tolerance is operational throughout life and is designed to control responses towards self antigens and foreign antigens which are not harmful. Peripheral T-cell tolerance can be induced and maintained by a variety of mechanisms, including deletion, induction of T-cell hypo-responsiveness, and differentiation of T regulatory (Tr) cells. Tr cells include a wide variety of cells with a unique capacity to inhibit effector T-cell responses. Although T cells with suppressive activity exist in all T-cell subsets, the best characterized are comprised in the $CD4^+$ T population. The two most relevant classes of Tr cells described within the $CD4^+$ subset to date are: T regulatory type 1 (Tr1) cells (1) and $CD4^+CD25^+$ Tr cells (2). These two Tr cell subsets differ in a number of important biological features, including their specific cytokine secretion profile, cellular markers, ability to differentiate in response to Ag specific stimuli, and dependency on cytokines versus cell-cell contact mechanisms for mediating suppressive activity.

IL-10 and Type 1 T Regulatory (Tr1) Cells.

IL-10 plays a central role in controlling inflammatory processes, suppressing T cell responses, and maintaining immunological tolerance (reviewed in (3)). IL-10 inhibits IFN-$\gamma$ and IL-2 production by T cells (4). It has anti-inflammatory effects inhibiting production of pro-inflammatory cytokines, such as TNF-$\alpha$, IL-1, and IL-6, and chemokines, such as IL-8 and MIP1$\alpha$, produced by activated antigen-presenting cells (APC), neutrophils, eosinophils, and mast cells. Furthermore, IL-10 down-regulates the expression of MHC class II, co-stimulatory, and adhesion molecules (5-7) on APC, and modulates their stimulatory capacity (8). Importantly, IL-10 is crucial for the differentiation of adaptive type 1 T regulatory (Tr1) cells (1). Tr1 cells are characterized by a unique cytokine secretion profile, upon TCR activation they secrete high levels of IL-10, significant amounts of IL-5, TGF-$\beta$ and low levels of IFN-$\gamma$, and IL-2 but not IL-4 (1). Ag-specific murine Tr1 cells can be indeed differentiated in vitro by repetitive TCR stimulation in the presence of high doses of IL-10 (1). Furthermore, treatment of mixed lymphocyte reaction (MLR) cultures with IL-10 (9) (and TGF-$\beta$ in the mouse (10)) results in T-cell anergy. Importantly, allo-reactive Tr1 cell clones from healthy individuals have been originally isolated by limiting dilution of in vitro IL-10-anergized $CD4^+$ T cells (1).

The first suggestion that human Tr1 cells are involved in maintaining peripheral tolerance in vivo came from studies in severe combined immunodeficient (SCID) patients successfully transplanted with HLA-mismatched allogenic stem cells. In the absence of immunosuppressive therapy, these patients do not develop GvHD. Interestingly, high levels of IL-10 are detected in the plasma of these patients and a significant proportion of donor-derived T cells, which are specific for the host HLA antigens and produce high levels of IL-10, can be isolated in vitro (11). Importantly, IL-10-anergized cells preserve their ability to proliferate in response to nominal antigens, such as Tetanus Toxoid and *Candida Albicans*, indicating that IL-10 induces an Ag-specific anergy (Bacchetta unpublished data). In a preclinical model of bone marrow transplantation, transfer of donor $CD4^+$ T cells anergized ex-vivo by host APC in the presence of IL-10 and TGF-$\beta$ results in a markedly decreased GvHD in MHC class II mismatched recipients (10, 12). These data offer a strong rationale for the development of a clinical protocol using co-transfer of ex-vivo IL-10-anergized cells of donor origin in patients undergoing haplo-identical HSC transplantation.

Tolerogenic Dendritic Cells (DC)

DC are highly specialized APC that classically initiate Ag-specific immune responses upon infection (13). This process involves the terminal maturation of DC, typically induced by agents associated with microbial infection. It is now clear that DC can be not only immunogenic but also tolerogenic. In steady state DC remains immature DC and can induce tolerance via deletion of Ag-specific effector T cells and/or differentiation of Tr cells (14-18). Repetitive stimulation of naïve cord blood $CD4^+$ T cells with allogeneic immature DC results in the differentiation of IL-10-producing Tr cells (19), which suppress T-cell responses via a cell-contact dependent mechanism. The authors recently reported that peripheral blood naïve CD4+ T cells stimulated with allogeneic immature DC become increasingly hypo-responsive to re-activation with mature DC and after three rounds of stimulation with immature DC, they are profoundly anergic and acquire regulatory function. These T cells are phenotypically and functionally similar to Tr1 cells since they secrete high levels of IL-10 and TGF-β, suppress T-cell responses via an IL-10- and TGF-β-dependent mechanism, and their induction can be blocked by anti-IL10 mAb (20). Not only immature DC but also specialized subsets of tolerogenic DC can drive the differentiation of Tr cells. Maturation and function of DC can be regulated at different levels (21). Both pharmacological and biological agents have been shown capable of inducing tolerogenic DC (22). Several biological agents including IL-10 (23, 24), TGF-β (25), IFN-α (26, 27), and TNF-α (28) can induce Tr cells. The presence of IL-10 during maturation of DC generate tolerogenic DC (23, 24), which express low levels of costimulatory molecules and MHC class II (24), display low stimulatory capacity (3, 29), and induce antigen-specific T cells anergy in both CD4+ and CD8+ T cells (23, 24).

It has been already described that IL-10 during DC differentiation results in a population of macrophage-like cells with low stimulatory capacity but mature phenotype (8, 30). Herein, we demonstrated that IL-10 treatment induces the differentiation of a unique subset of DC (Tr-DC) characterized by the expression of CD14, CD11c, CD11b, CD83, CD80, CD86, CD71 and HLA-DR, but not CD1a. Tr-DC express immunoglobulin-like transcript (ILT) 2, ILT-3, ILT-4, and the non classical MCH class I molecule HLA-G. Tr-DC secrete significantly higher levels of IL-10 compared to immature DC, whereas the amounts of IL-12 are comparable to those produced by immature DC. Interestingly, IL-10/IL-12 ratio is maintained upon activation with LPS and IFN-γ. Tr-DC display lower stimulatory capacity compared to immature DC, and, importantly, induce Tr1 cells. Thus, IL-10 promote the differentiation of a new subset of tolerogenic DC which can be used to generate anergic Tr1 cells with limited in vitro manipulation and suitable for potential clinical use to restore peripheral tolerance.

Induction of T cell anergy by IL-10-treated DC has been suggested by Zheng et al. (2004). The authors have generated immature DC by culture of adherent cells with IL-4 and GM-CSF treatment. The immature DC obtained after 7 days are then washed and cultured with IL-10 for additional 2 days. The resulting IL-10-treated immature DC present a phenotype very different from the one of the Tr-DC obtained in the present invention. Indeed, the cells obtained in Zheng et al. are CD83 negative, CD86 low and HLA-DR low.

The protocol proposed by Levings et al. (2005) leads to the induction of Tr1 cells by repetitively stimulation of CD4+ T cells using immature DC, which are different from the Tr-DC generated in the present invention.

The international patent application WO2004/087899 discloses a method for obtaining Tr1 cells from T cells by means of specialized DC. DC are obtained from CD34+ cells in presence of IL-4, GM-CSF and IL-10. However, by contrast with the Tr1 DC of the present invention, the resulting DC express low level of CD11c, HLA-DR, CD80 and CD86, and are CD14 negative.

The international patent application WO03/000199 provides compositions which comprise at least two of a CD4+CD25+ T cell, IL-10, a CD8+CD28− cell and a vitamin D3 analog. This application also discloses a method for generating a tolerogenic antigen-presenting cell, which comprises contacting the cell with an effective amount of IL-10, a CD4+CD25+ T cell and/or a vitamin D3 analog. A method for increasing the expression of ILT3 and/or ILT4 by an antigen-presenting cell which comprises contacting the cell with an effective amount of IL-10, a CD4+CD25+ cell and/or a vitamin D3 analog and methods for inhibiting the onset of or treating the rejection of an antigenic substance and inhibiting the onset of or treating an autoimmune disease in a subject are provided.

The U.S. Pat. No. 6,277,635 describes IL-10 for producing a population of cells which are capable of inhibiting or suppressing reactions to alloantigens, for example in graft-versus-host disease or tissue rejection. IL-10 for reducing responses in mixed lymphocyte response (MLR) is also described. Exogenous or induced endogenous IL-10 may be used for the inhibition or suppression of the reactions to alloantigens. The Tr-DC method of the present invention differs from the IL-10 protocol to anergize T cells in vitro as follow:

Anergy by Tr-DC can be induced in all the individuals.
Anergic T cells induced by Tr-DC are more stable compared to those obtained with IL-10.
T-cell cultures obtained with Tr-DC display higher cell recovery compared to those obtained with IL-10.
IL-10 and Tr-DC are comparable in inducing T-cell anergy in haplo-identical pairs. Importantly, in haplo-identical pairs in which IL-10 does not induce anergy, Tr-DC do.
In HLA-matched un-related (MUD) pairs the use of DC is required to stimulate host-specific T-cell responses, therefore Tr-DC are necessary for T-cell anergy induction.
Lower number of cells from both recipient and donor are required for the in vitro manipulation to generate anergized T cells with the Tr-DC of the present invention.

The United States patent application 20070009497 relates to culture-expanded T suppressor cells and their use in modulating immune responses. This invention provides methods of producing culture-expanded T suppressor cells, which are antigen specific, and their use in modulating complex autoimmune diseases. In particular a method for producing an isolated, culture-expanded T suppressor cell population, comprising: (a) contacting CD25+CD4+ T cells with DC and an antigenic peptide, an antigenic protein, or a derivative thereof, or an agent that cross-links a T cell receptor on said T cells in a culture, for a period of time resulting in antigen-specific CD25+CD4+ T cell expansion; and (b) isolating the expanded CD25+CD4+ T cells obtained in (a), thereby producing an isolated, culture-expanded T suppressor cell population is provided. The DC population describes in this application display very different characteristics than the Tr-DC population of the present invention.

The International patent application WO03102162 relates to tolerogenic DC and methods for enriching for these cells in tissue preparations and using the cells for preventing or minimizing transplant rejection or for treating or preventing an autoimmune disease. A human tolerogenic DC having surface antigens DEC205 and B220, but not CD19 is described.

HLA-G and Immunomodulatory Properties

HLA-G, a non-classical MHC class I molecules, is a low polymorphic molecule. Compared with the classical class I genes, the most polymorphic genes in the human genome, HLA-G has relatively little polymorphism in its coding region (31). The HLA-G gene has eight exons encoding a signal peptide (exon 1), the α1, α2, and α3 domains (exons 2, 3, and 4, respectively), the transmembrane domain (exon 5), and the intracellular domain (exons 6 and 7), similar to other class I genes. However, a premature stop codon in exon 6 results in a truncated cytoplasmic tail that reveals a cryptic retrieval motif (32). This results in the slow turnover and prolonged expression of HLA-G at the cell surface. HLA-G encodes multiple isoforms as a result of alternative splicing. The full-length isoform HLA-G1 is structurally similar to other class I genes, except for the truncated cytoplasmic tail. The G2 isoform results from the removal of exon 3 and homodimerizes to form an HLA class II-like structure (33). HLA-G1 and HLA-G2 isoforms can be also expressed as soluble proteins (HLA-G5 and -G6, respectively) due to the inclusion of intron 4 sequences in the mature mRNA, resulting in secreted proteins with an additional 21 amino acids (encoded by intron 4 sequences) following the α3 domain (34). HLA-G3 results from the removal of exons 3 and 4. Additional isoforms are HLA-G4 and -G7.

HLA-G has been extensively studied in pregnancy and it is known to be the major contributor to induction and maintenance of foetal-maternal tolerance (31, 35). HLA-G inhibits cytolytic activities of both NK and CTL (36), and allo-specific T-cell proliferation (37, 38). A positive correlation between allograft acceptance and HLA-G expression on both graft cells (39, 40) and T cells (38) has been reported (41), indicating a role of HLA-G in modulating allo-responses. In addition, HLA-G acts as a negative regulator of tumor immune responses through several mechanisms including, inhibition of angiogenesis, prevention of antigen recognition and T-cell migration, and suppression of T and NK cytolytic effects (42). Antigen-presenting cells expressing HLA-G1 are poor stimulators and are able to promote the induction of anergic/suppressor $CD4^+$ T cells (43). Moreover, HLA-G binds to the inhibitory molecules immunoglobulin-like transcript (ILT)-2 and ILT-4 expressed on DC (39, 44). It has been shown that engagement of ILT-4 by HLA-G prevents the up-regulation of costimulatory molecules, inhibits DC maturation (45), and promotes the differentiation of anergic/suppressor $CD4^+$ T cells (46). The authors demonstrated that soluble HLA-G alone or in combination with IL-10 promotes the differentiation of a population of $CD4^+$ T cells with low proliferative capacity and suppressor functions. Soluble HLA-G-induced Tr cells produce TGF-β, intermediate levels of IL-10 and IFN-γ, but low levels of IL-2, and IL-4, express high levels of granzyme B, CTLA4, CD25, but not FOXP3. Thus soluble HLA-G is a new immunomodulatory compound able to promote the differentiation of a population of CD4+ T cells with regulatory activity.

SUMMARY OF INVENTION

In the present invention the following nomenclature was used:

Tr1 for Type 1 T regulatory, iDC for immature dendritic cells, Tr-DC for dendritic cells generated in the presence of exogenous IL-10. Tr-Dc may be also called Tr1-DC, DC-10, and IL-10 DC. mDC for mature dendritic cells, T(iDC) for T cell lines generated by stimulating naïve $CD4^+$ T cells or PBMC with allogeneic immature DC, T(Tr-DC) for T cell lines generated by stimulating naïve $CD4^+$ T cells or PBMC with Tr-DC, T(mDC) for T cell lines generated by stimulating naïve $CD4^+$ T cells or PBMC with mature DC, T(MLR) for T cell lines generated by stimulating PBMC with allogenic CD3 depleted cells, T(MLR/IL-10) for T cell lines generated by stimulating PBMC with allogenic CD3 depleted cells in the presence of exogenous IL-10, Th0 for T cell lines differentiated in vitro in the presence of exogenous IL-2, Tg for T cell lines differentiated in vitro in the presence of soluble HLA-G, Tg10 for T cell lines differentiated in vitro in the presence of exogenous IL-10 and soluble HLA-G.

The present invention relates to a method to generate T cells having regulatory activity in particular, Tr1 cells using a unique population of dendritic cells named Tr-DC. Furthermore, the ability of soluble HLA-G to promote the differentiation of regulatory T cells is disclosed. The potential to generate T cells having regulatory activity to be used as cellular therapy in the clinical context of allogeneic HSC transplantation, organ transplantation, autoimmune diseases, chronic inflammatory diseases, allergies, and asthma with limited in vitro manipulation is valuable.

It is therefore an object of the invention a tolerogenic dendritic cell population (Tr-DC) having the following marker phenotype: $CD14^+$, $CD11c^+$, $CD11b^+$, and $CD1a^-$. Preferably, the tolerogenic dendritic cell population (Tr-DC) is further $CD83^+$, $CD80^+$, $CD86^+$, $HLA-DR^+$, $CD71^+$. More preferably the tolerogenic dendritic cell population is further $ILT-2^+$ and/or $ILT-3^+$ and/or $ILT-4^+$ and/or $HLA-G^+$.

Even more preferably, the tolerogenic dendritic cell population (Tr-DC) is capable to generate a population of T cells having regulatory activity. Preferably the population of T cells having regulatory activity is a population of Tr1 cells.

It is an object of the invention an in vitro method for generating a population of tolerogenic dendritic cells (Tr-DC) as defined above comprising the steps of:
a) collecting PBMCs from a subject;
b) isolating adherent cells from collected PBMCs;
c) exposing said isolated adherent cells under appropriate culture conditions to an effective amount of GM-CSF, IL-4 and IL-10 or functional derivatives thereof.

Preferably said adherent cells are mainly $CD14^+$ monocytes. Preferably the step of isolating adherent cells and exposing said isolated adherent cells under appropriate culture conditions, is performed in the presence of fetal calf serum (FCS) or of human serum (HS). Preferably, the effective amount of GM-CSF is between 1-1000 ng/ml. Preferably, the effective amount of IL-4 is between 1-1000 ng/ml. Preferably, the effective amount of IL-10 is between 1-1000 ng/ml.

It is a further object of the invention a method for isolating a population of tolerogenic dendritic cells (Tr-DC) as described above comprising the steps of:
a) collecting a sample from a subject;
b) isolating the sample cells with at least one of markers included in the group of: CD14, CD11c, CD11b, CD83, CD80, CD86, HLA-DR, CD71, ILT-2, ILT-3, ILT-4 or HLA-G.

Preferably, the sample is a blood, a spleen or a lymph node sample.

It is an object of the invention, the use of the population of tolerogenic dendritic cells Tr-DC as described above for generating a population of T cells having regulatory activity. Preferably, the population of T cells having regulatory activity is a population of Tr1 cells. It is a further object of the invention an in vitro method for generating a population of T cells having regulatory activity comprising the steps of:
a) irradiating the Tr-DC cell population described above;
b) isolating PBMCs from a subject;
d) stimulating said isolated PBMCs in appropriate culture conditions with an effective amount of said irradiated Tr-DC cell population.

Preferably, in the in vitro method, the population of T cells having regulatory activity is a population of Tr1 cells.

It is another object of the invention, a population of Tr1 cells obtainable by the method described above being:
a) anergic;
b) T cell response suppressive;
c) DC response suppressive; and
d) having the following marker phenotype: $IL-10^{++}$, $TGF-β^+$, $IL-4^-$ and IFN-γ and IL-2 negative to low.

It is another object of the invention, the use of the population of T cells having regulatory activity obtainable according to the method above to induce or restore immune tolerance in a subject.

It is a further object of the invention, the use of the population of T cells having regulatory activity obtainable according to the method described above for the preparation of a medicament for the prevention and/or treatment of graft versus host disease, and/or of organ rejection, and/or of autoimmune diseases, and/or of allergies, and/or of asthma, and/or of chronic inflammatory diseases. Preferably, the autoimmune diseases are comprised in the group of: type 1 diabetes mellitus, autoimmune entheropathy, rheumatoid arthritis, systemic lupus erythematosus, multiple sclerosis or psoriasis. Preferably, the chronic inflammatory diseases are comprised in the group of: inflammatory bowel disease, Chron's disease or vasculitis. More preferably allergies comprise atopic dermatitis.

It is a further object of the invention the use of the population of T cells having regulatory activity obtainable according to the method above for the preparation of a medicament for the prevention and/or treatment of immune responses induced by gene therapy products. Another object of the invention is the use of the population of T cells having regulatory activity obtainable according to the method above for the treatment of genetic autoimmune diseases comprised in the group of: immune dysfunction, Polyendocrinopathy Enteropathy X-linked (IPEX) syndrome, Autoimmune Polyendocrinopathy-Candidiasis-Ectodermal Dystrophy (APECED) syndrome, and OMENN's syndrome.

Preferably, the population of T cells having regulatory activity is a population of Tr1 cells. Another object of the invention is the use of the tolerogenic dendritic cell population (Tr-DC) as described above to induce or restore immune tolerance in a subject.

It is also an object of the invention the use of the tolerogenic dendritic cell population (Tr-DC) for the preparation of a medicament for the prevention and/or treatment of graft versus host disease, and/or of organ rejection, and/or of autoimmune diseases, and/or of allergies, and/or of asthma, and/or of chronic inflammatory diseases. Preferably the autoimmune diseases are comprised in the group of: type 1 diabetes mellitus, autoimmune entheropathy, rheumatoid arthritis, systemic lupus erythematosus, multiple sclerosis or psoriasis. Preferably the chronic inflammatory diseases are comprised in the group of: inflammatory bowel disease, Chron's disease or vasculitis. Preferably, allergies comprise atopic dermatitis.

It is a further object of the invention, the use of the tolerogenic dendritic cell population (Tr-DC) as described above for the preparation of a medicament for the prevention and/or treatment of immune responses induced by gene therapy products.

It is another object of the invention, the use of the tolerogenic dendritic cell population (Tr-DC) as described above for the treatment of genetic autoimmune diseases comprised in the group of: immune dysfunction, Polyendocrinopathy Enteropathy X-linked (IPEX) syndrome, Autoimmune Polyendocrinopathy-Candidiasis-Ectodermal Dystrophy (APECED) syndrome, and OMENN's syndrome.

It is an object of the invention the use of HLA-G as a tolerogenic biomarker of Tr-DC.

It is a further object of the invention the use of soluble HLA-G to generate a population of T cells having regulatory activity.

It is another object of the invention the use of soluble HLA-G to induce or restore immune tolerance in a subject and the use of soluble HLA-G for the preparation of a medicament for the prevention and/or treatment of graft versus host disease, and/or of organ rejection, and/or of autoimmune diseases, and/or of allergies, and/or of asthma, and/or of chronic inflammatory diseases.

Preferably soluble HLA-G is soluble HLA-G1 and/or HLA-G5.

In the methods of the invention, the subject from whom Tr-DC are generated may be different from the subject from whom PBMCs are isolated. The subject from whom PBMCs are isolated may be a recipient in the case of hematopoietic stem cell transplantation, a donor in the case of organ transplantation, or a self in the case of autoimmunity, allergies, asthma, and chronic inflammatory diseases. The methods of the present invention are independent on the degree of HLA disparities between the Tr-DC and PBMCs cells used.

The invention will be now described by means of non limiting examples referring to the following figures:

FIG. 1. Tr-DC: morphology and phenotype. Monocyte-derived DC were differentiated in IL-4 and GM-CSF in the presence of IL-10 (Tr-DC) for 7 days, or in IL-4 and GM-CSF for 5 days and cultured for additional 2 days with (mature DC) or without (immature DC) LPS. A. Morphology of DC was evaluated by microscopy. B. Expression of CD1a, CD14, CD83, HLA-DR, CD11c, CD11b, CD71, CD80, and CD86 was evaluated by FACS analysis. A representative donor out of twenty tested in independent experiments is presented. C-D. Tr-DC produce high levels of IL-10 but low amounts of IL-12. Immature (iDC), DC differentiated with IL-10 (Tr-DC), and mature DC (mDC) were cultured (C) alone or (D) activated with IFN-γ (50 ng/ml) and LPS (200 ng/ml). Culture supernatants were collected 48 h after culture, and levels of secreted IL-12 and IL-10 were determined by ELISA. The average±SEM amounts detected in five independent experiments are presented. *$P \leq 0.05$ and **$P \leq 0.005$ as indicated.

Figure 2:
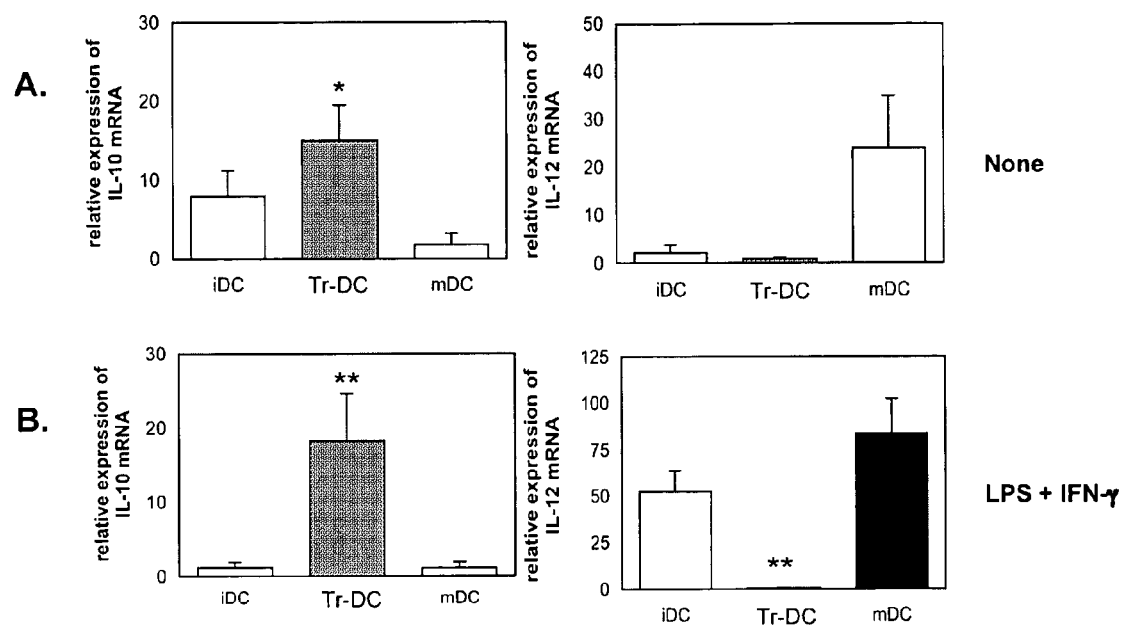

FIG. 2. Expression of mRNA for IL-10 and IL-12 in iDC, Tr-DC, and mDC (A) left inactivated or (B) activated with IFN-γ (50 ng/ml) and LPS (200 ng/ml), were compared for. Relative levels of IL-10 and IL-12 expression were determined by quantitative RT-PCR. The amounts of IL-10 and IL-12 mRNA are expressed as relative to non-activated PBMC (which were given an arbitrary value of 1). The average±SEM amounts detected in six independent experiments are presented. *$P<0.05$, and **$P<0.005$ when compared to iDC.

Figure 3:
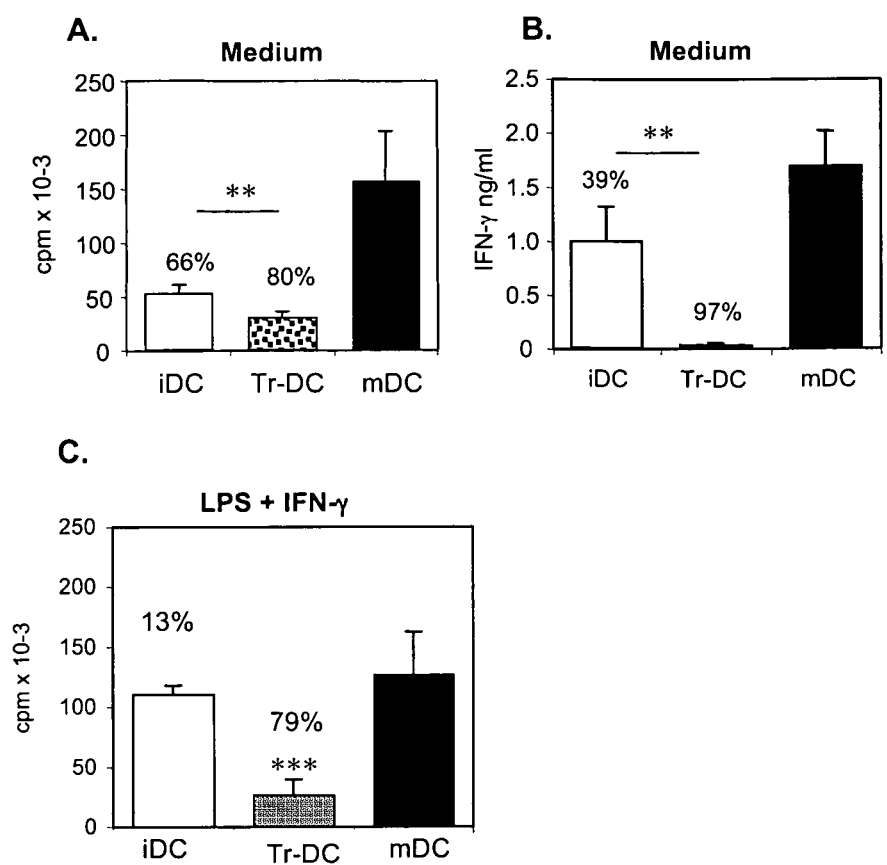

FIG. 3. Tr-DC display low stimulatory capacity. A. Naïve CD4$^+$ T cells were cultured with allogeneic immature (iDC), DC differentiated in the presence of IL-10 (Tr-DC), and mature DC (mDC) at the ratio of 10:1. Proliferate responses were evaluated 4 days after culture by [$^3$H]-thymidine incorporation for an additional 16 h. B. In parallel, supernatants were collected after 48 h and IFN-γ analyzed by ELISA. C. Activated Tr-DC maintain low stimulatory capacity. Allogeneic iDC, Tr-DC, and mDC, activated with IFN-γ (50 ng/ml) and LPS (200 ng/ml) for 48 h, were cultured with naïve CD4$^+$ T cells at the ratio of 1:10. Proliferative responses were evaluated 4 days after culture by [$^3$H]-thymidine incorporation for an additional 16 h. Results of one representative experiment of twenty-four (A), four (B), and eight (C) independent experiments performed are shown. Numbers represent the % of inhibition of proliferation of T cells primed with iDC or Tr-DC compared to proliferation of T cells stimulated with mDC (A, C), the % of inhibition of IFN-γ production by T cells primed with iDC or Tr-DC compared to that obtained in T cells stimulated with mDC (B). **$P \leq 0.005$ when naïve CD4$^+$ T cells primed with Tr-DC were compared to naïve CD4$^+$ T cells primed with iDC.

Figure 4:
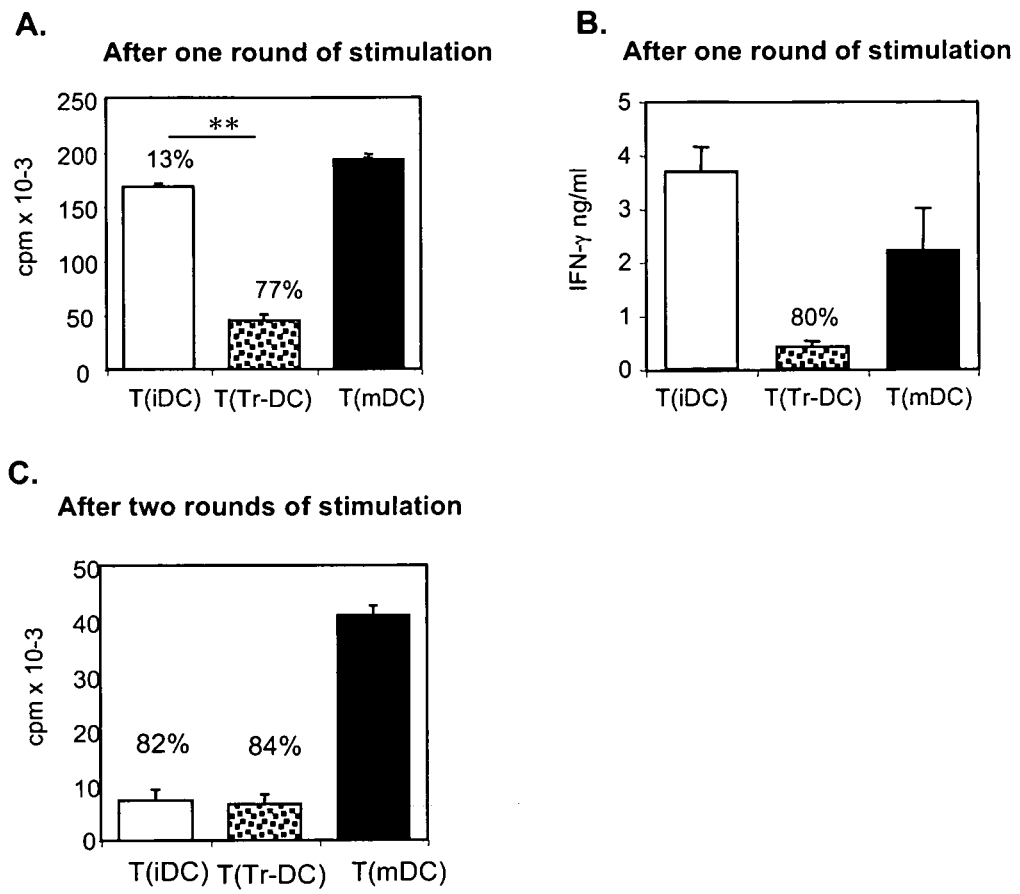

FIG. 4. Tr-DC induce T-cell anergy. A. To generate anergic T cells, naïve CD4+ T cells were stimulated with allogeneic iDC [T(iDC)], Tr-DC [T(Tr-DC)], or mDC [T(mDC)] for one or two rounds of stimulation. After one round (A, B) and two rounds (C) of stimulation, T(iDC), T(Tr-DC), and T(mDC) cell lines were tested for their ability to proliferate in response to mDC from the same allogeneic donor. Proliferative responses were evaluated 2 days after culture by [$^3$H]-thymidine incorporation for an additional 16 h. B. In parallel, supernatants were collected after 48 h and analyzed by ELISA to determine levels of IFN-γ. Results of one representative experiment of twenty-four (A), three (B), and eight (C) independent experiments performed are shown. Numbers represent the % of anergy of T(iDC) or T(Tr-DC) cell lines compared to T(mDC) cell lines. **P≤0.005 when T(Tr-DC) cell lines were compared to T(iDC) cell lines.

Figure 5:
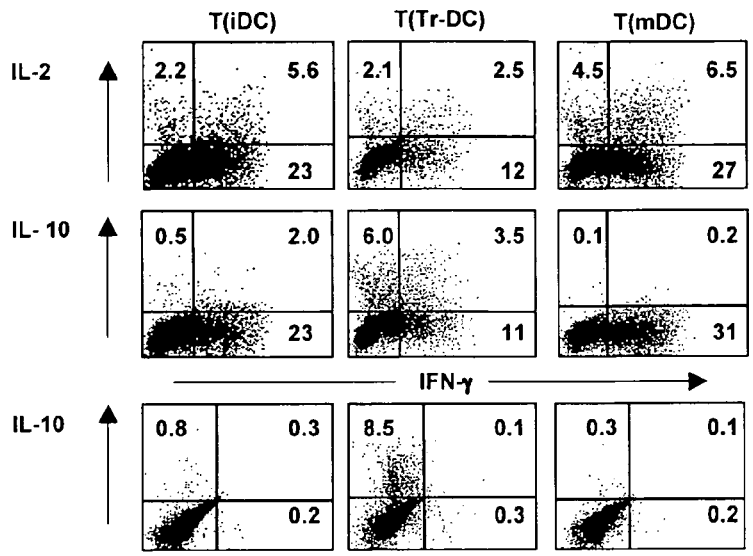
Figure 5:
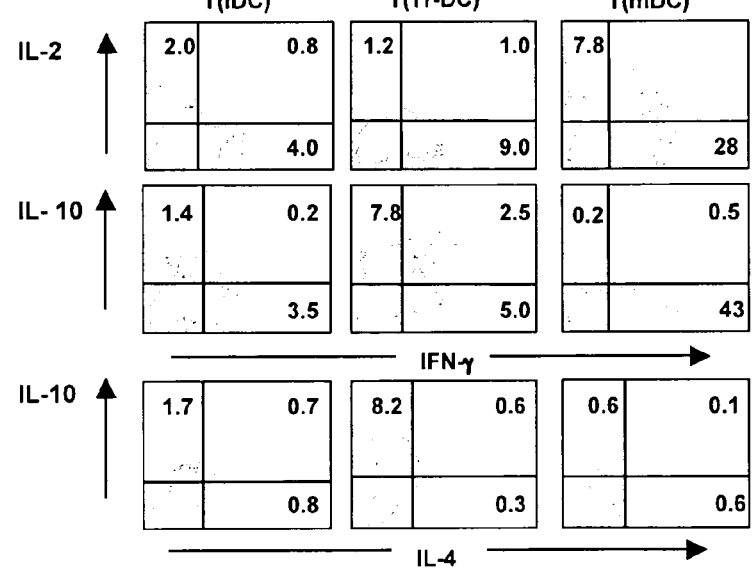
Figure 5:
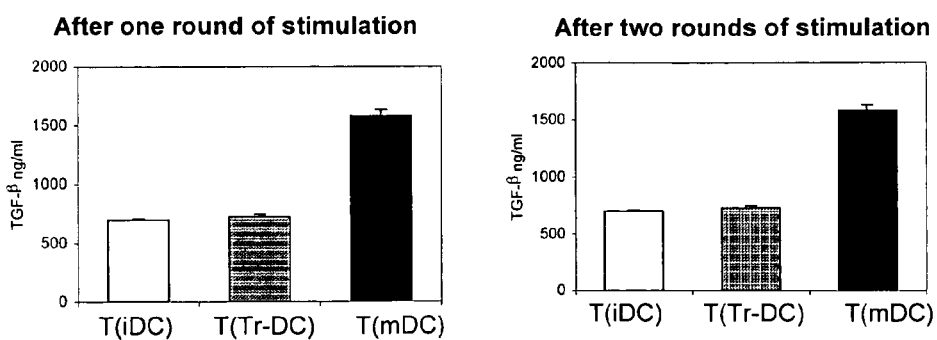

FIG. 5. Tr-DC induce Tr1 cells. Naïve CD4+ T cells were stimulated with allogeneic iDC [T(iDC)], Tr-DC [T(Tr-DC)], or mDC [T(mDC)] one or two rounds of stimulation. At the end of one (A) or two (B) rounds of stimulation T cell lines were restimulated with immobilized anti-CD3 mAb (10 μg/ml) and TPA (1 ng/ml), and cytokine production was determined by intracytoplasmic staining and cytofluorometric analysis, as described in Materials and Methods. One representative experiment out of nine (A) or three (B) is presented. C. At the end of each round of stimulations with immature [T(iDC)], Tr-DC [T(Tr-DC)] and mature DC [T(mDC)], T-cell lines were activated with mDC and supernatants were collected after 72 h of culture. Levels of for TGF-β were determined by ELISA. The average±SEM amounts detected in five independent experiments are presented.

Figure 6:
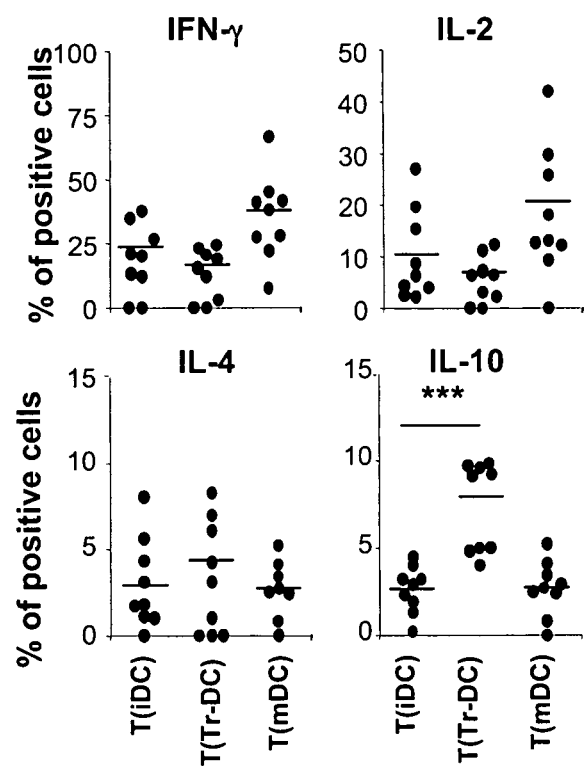

FIG. 6. Tr-DC induce Tr1 cells. Naïve CD4+ T cells were stimulated with allogeneic iDC [T(iDC)], Tr-DC [T(Tr-DC)], or mDC [T(mDC)] for 14 days (one round of stimulation). After stimulation, T-cell lines were activated with immobilized anti-CD3 mAb and TPA, and cytokine production was determined by intracytoplasmic staining and cytofluorometric analysis. Percentages of IFN-γ, IL-2-, IL-4-, and IL-10-producing cells in T(iDC), T(Tr-DC), and T(mDC) cell lines generated from each of the nine donors tested are presented. ***P≤0.001 when T(Tr-DC) cell lines were compared to T(iDC) cell lines.

Figure 7:
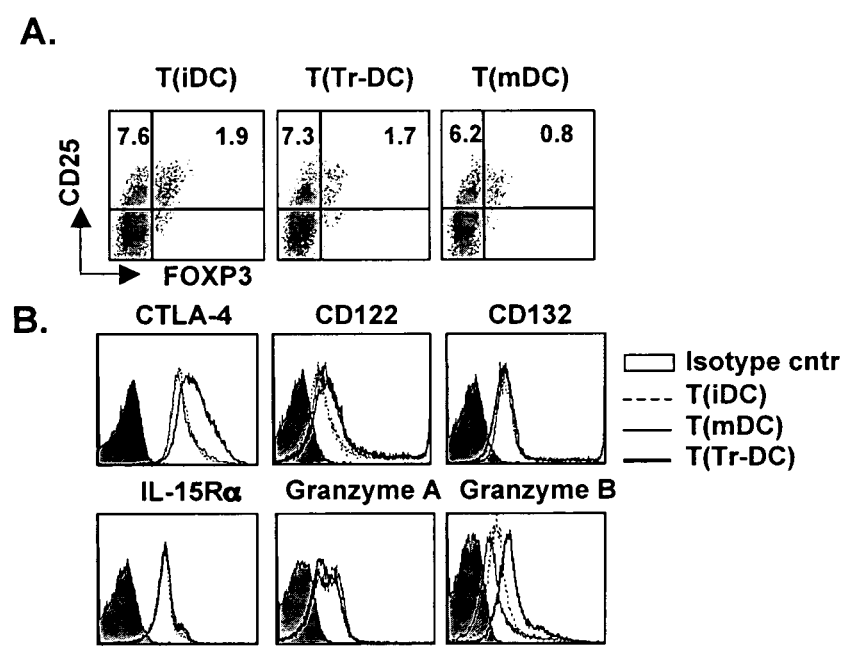

FIGS. 7A-7B. Phenotype of T cells generated with Tr-DC. T(iDC), T(Tr-DC), and T(mDC) cell lines was analyzed 14 days after culture for the expression of the indicated markers. Results from one representative donor out of nine tested are presented.

Figure 8:
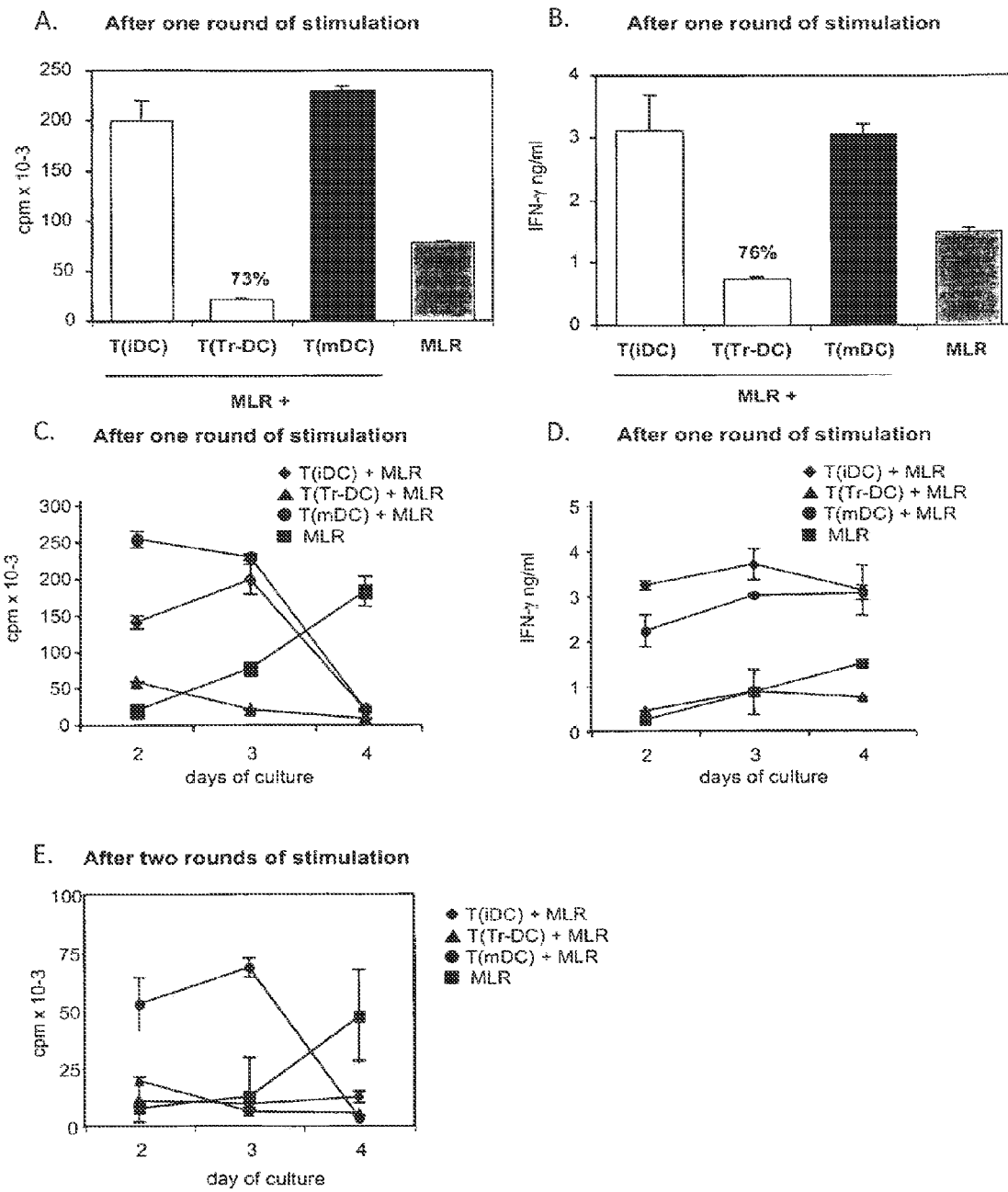

FIG. 8. Tr-DC are more powerful than immature DC to generate Tr1 cells. Naive CD4+ T cells were stimulated with allogeneic immature [T(iDC)], [T(Tr-DC)] and mature DC [T(mDC)] for one or two rounds of stimulation. A. After one round of stimulation, T-cell lines were tested for their ability to suppress responses of autologous CD4+ T cells activated with mDC (MLR). Naïve CD4+ T cells were stimulated with mDC alone (MLR) or in the presence of T(iDC), T(Tr-DC), and T(mDC) cell lines at a 1:1 ratio. [$^3$H]-thymidine was added after 3 days of culture for an additional 16 h. Results of one experiment representative of eight independent experiments are shown. B. Suppression of IFN-γ production by CD4+ T cells in response to mDC was measured in culture supernatants after 4 days of culture. Results representative of three independent experiments are shown. C-D. Kinetic of suppression by T(Tr-DC) cells. Naïve CD4+ T cells were stimulated with allogeneic iDC [T(iDC)], Tr-DC [T(Tr-DC)], or mDC [T(mDC)] for one or two rounds of stimulation. After one (C) and two (E) rounds of stimulation, T-cell lines were tested for their ability to suppress responses of autologous CD4+ T cells activated with mDC (MLR). Naïve CD4+ T cells were stimulated with mDC alone (MLR) or in the presence of T(iDC), T(Tr-DC), and T(mDC) cell lines at a 1:1 ratio. [$^3$H]-thymidine was added at day 2, 3, and 4 for an additional 16 h. Results of one experiment representative of eight independent experiments are shown. D. After one round of stimulation, T cell lines were tested for their ability to suppression of IFN-γ production by CD4+ T cells in response to mDC. Results representative of three independent experiments are shown.

Figure 9:
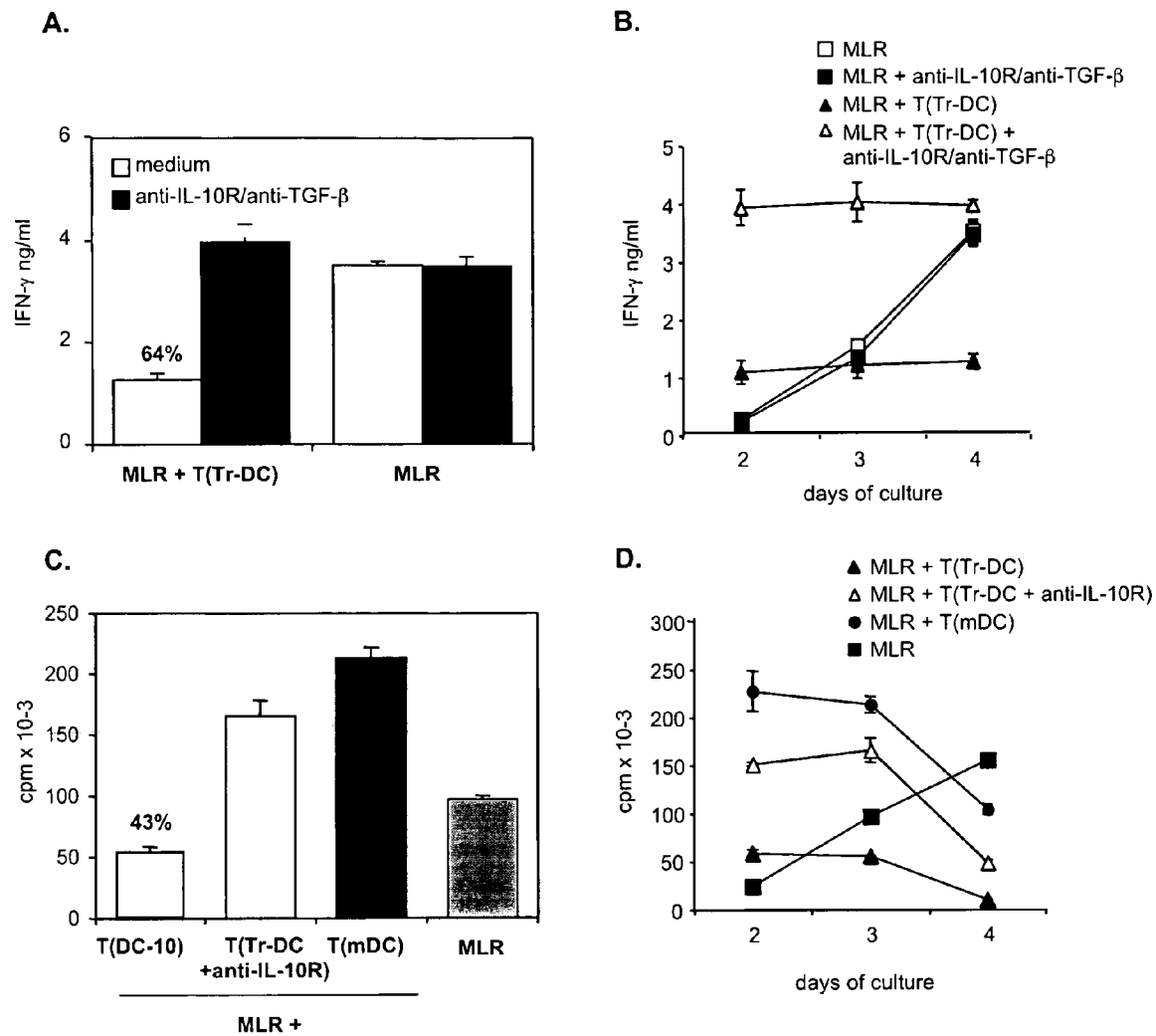

FIG. 9 A-B. Role of IL-10 and TGF-β in suppression mediated by T(Tr-DC) cell lines. T(Tr-DC) cell lines were tested for their ability to suppress IFN-γ production of CD4+ T cells in response to allogeneic monocytes in the absence or presence of anti-IL-10R and anti-TGF-β mAbs. Suppression of IFN-γ production was measured in culture supernatants 2 (B), 3 (B), and 4 (A, B) days after culture. Results are representative of three independent experiments. C-D. Autocrine IL-10 is required for the differentiation of T(Tr-DC) cells with regulatory activity. Naive CD4+ T cells were stimulated with allogeneic Tr-DC in the presence of anti-IL10R or control IgG mAbs. After activation, T cells were collected and tested for their ability to suppress the response of autologous CD4+ T cells activated with mDC (MLR). [$^3$H]-thymidine was added at day 2 (D), 3 (D), and 4 (C, D) for an additional 16 h. Results of one experiment representative of three independent experiments are shown.

Figure 10:
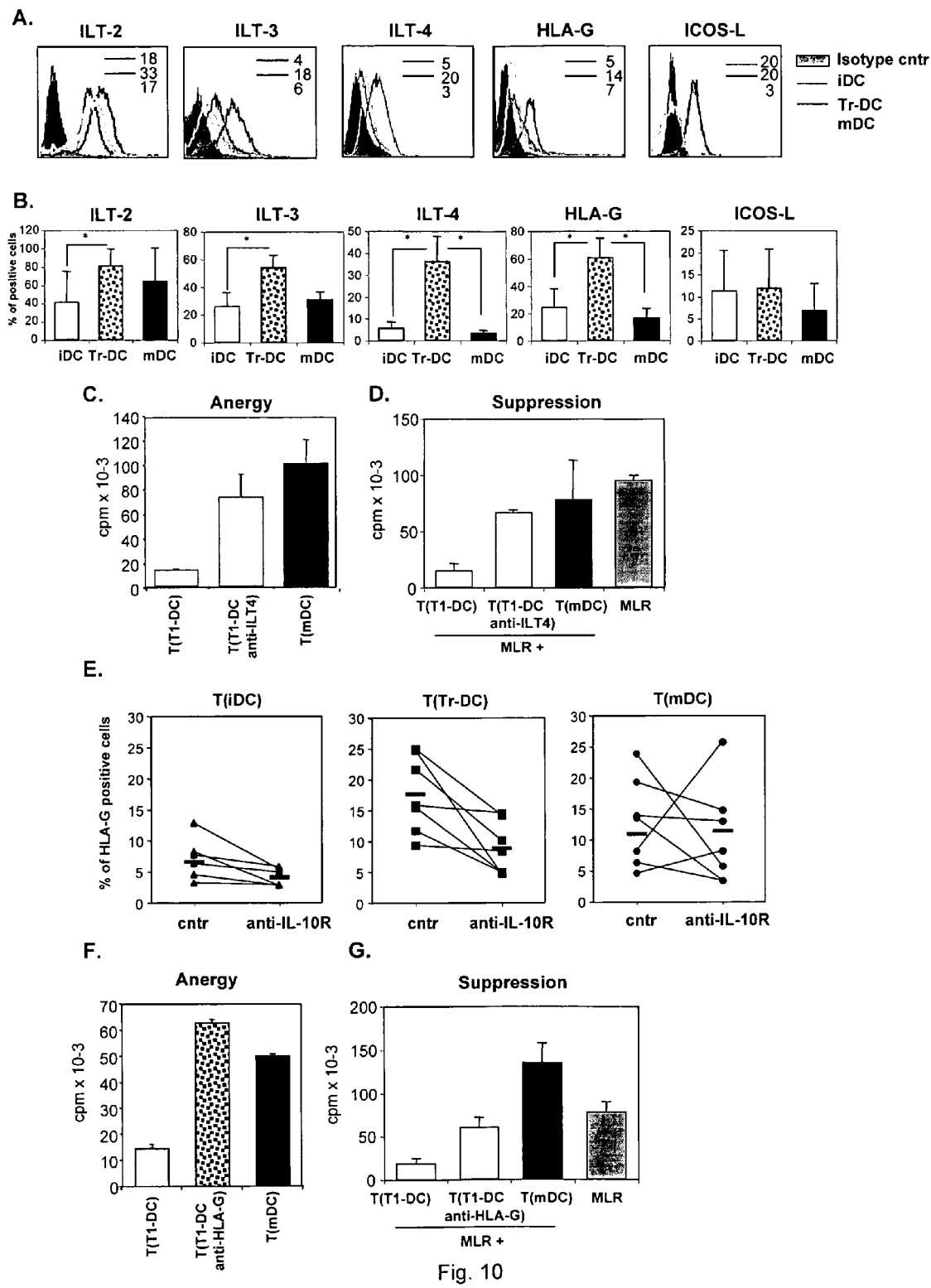

FIG. 10. Tr-DC express tolerogenic markers. Monocyte-derived DC were differentiated in IL-4 and GM-CSF in the presence of IL-10 (Tr-DC) for 7 days, or in the absence of IL-10 for 5 days and activated for additional 2 days with (mDC) or without (iDC) LPS. A. DC were analyzed by flow cytometry to determine levels of expression of ILT-2, ILT-3, ILT-4, HLA-G, and ICOS-L. B. Mean percentages of positive cells, set according to the isotype-matched controls, gated on CD11c+ cells (not shown), ±SD are shown. *P<0.01 when TR-DC were compared to iDC and mDC. C-G. Induction of Tr1 cells requires ILT-4/HLA-G interaction. Naïve CD4+ T cells were stimulated with Tr-DC in presence of anti-ILT-4 [T(Tr-DC anti-ILT-4)] or control IgG [T(Tr-DC)] mAbs. As control, naïve CD4+ T cells were stimulated with mDC [T(mDC)]. After stimulation, T cell lines were collected and tested for their ability to proliferate in response to mDC (C) and to suppress responses of autologous CD4+ T cells activated with mDC (MLR) (D). [$^3$H]-thymidine was added after 2 days (C), and 4 days (D) of culture for an additional 16 h. Results are representative of four independent experiments. E. IL-10 induces up-regulation of HLA-G on naïve T cells. Naïve CD4+ T cells were stimulated with iDC, Tr-DC, and mDC for 48 hours in the presence of control IgG or anti-IL-10R mAbs. T cells were analyzed by flow cytometry to determine levels of expression of HLA-G. Percentages of CD4+ HLA-G+ T cells are shown. Red lines represent the mean percentages of CD4+HLA-G+ T cells. F-G. Naïve CD4+ T cells were stimulated with Tr-DC in the presence of anti-HLA-G [T(Tr-DC anti-HLA-G)] or control IgG [T(Tr-DC)] mAbs. As control, naïve CD4+ T cells were stimulated with mDC [T(mDC)]. After stimulation, T cell lines were collected and tested for their ability to proliferate in response to mDC (F) and to suppress responses of autologous CD4+ T cells activated with mDC (MLR) (G). [$^3$H]-thymidine was added after 2 days (F), and 4 days (G) of culture for an additional 16 h. Results are representative of three independent experiments.

Figure 11:
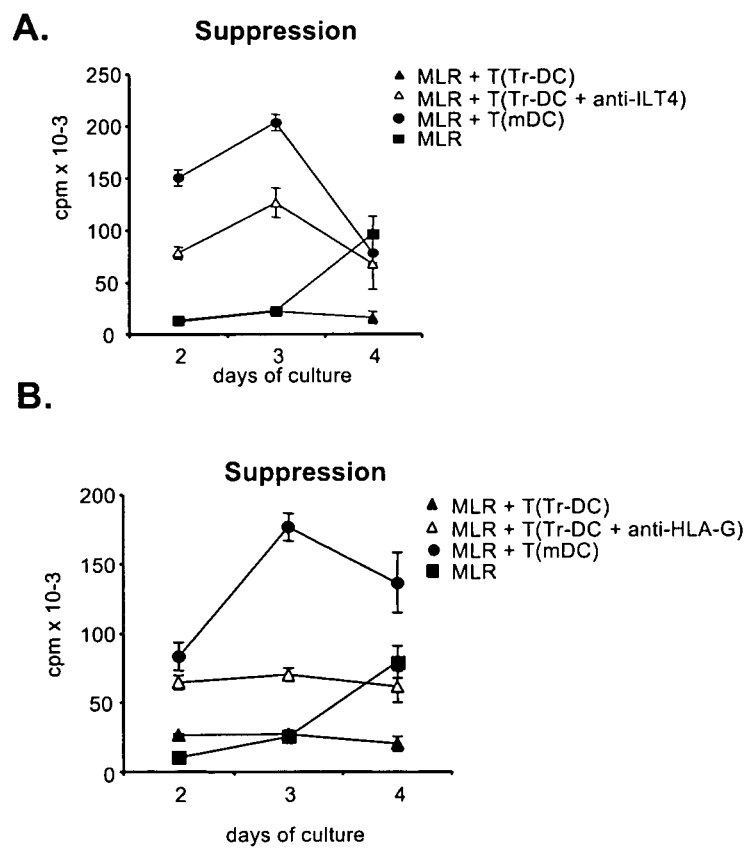

FIG. 11. Kinetic of suppression by T(Tr-DC) cells in the presence of anti-ILT-4 or anti-HLA-G mAbs. A. Naïve CD4+

T cells were stimulated with Tr-DC in presence of anti-ILT-4 [T(Tr-DC+anti-ILT-4)] or control IgG [T(Tr-DC)] mAbs. As control, naïve CD4+ T cells were stimulated with mDC [T(mDC)]. After stimulation, T cell lines were collected and tested for their ability to suppress responses of autologous CD4+ T cells activated with mDC (MLR). [$^3$H]-thymidine was added after 2, 3, and 4 days of culture for an additional 16 h. Results are representative of four independent experiments. B. Naïve CD4+ T cells were stimulated with Tr-DC in the presence of anti-HLA-G [T(Tr-DC+anti-HLA-G)] or control IgG [T(Tr-DC)] mAbs. As control, naïve CD4+ T cells were stimulated with mDC [T(mDC)]. After stimulation, T cell lines were collected and tested for their ability to suppress responses of autologous CD4+ T cells activated with mDC (MLR). [$^3$H]-thymidine was added after 2, 3, and 4 days of culture for an additional 16 h. Results are representative of three independent experiments.

Figure 12:
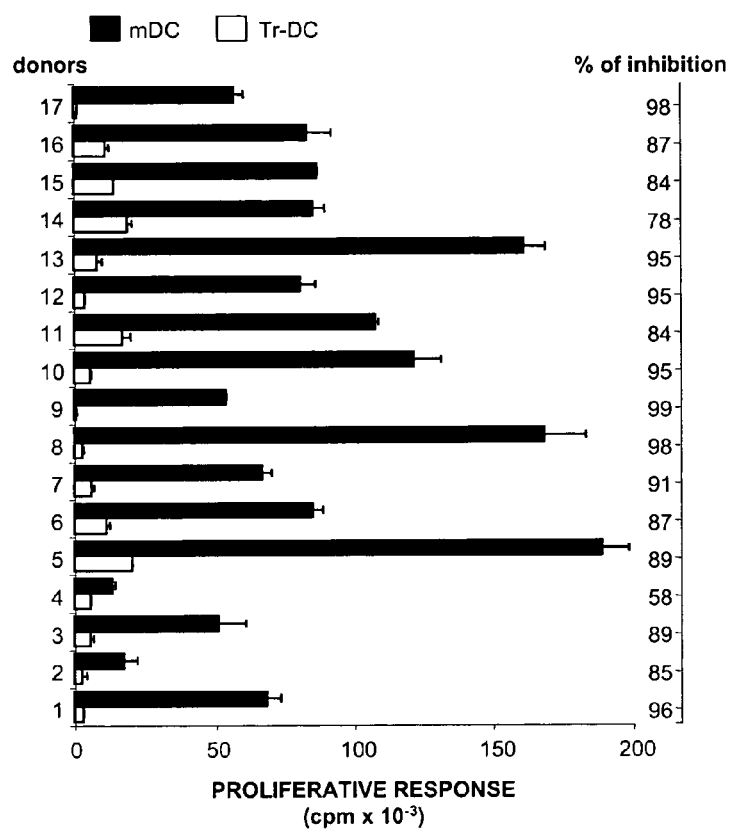
Figure 12:
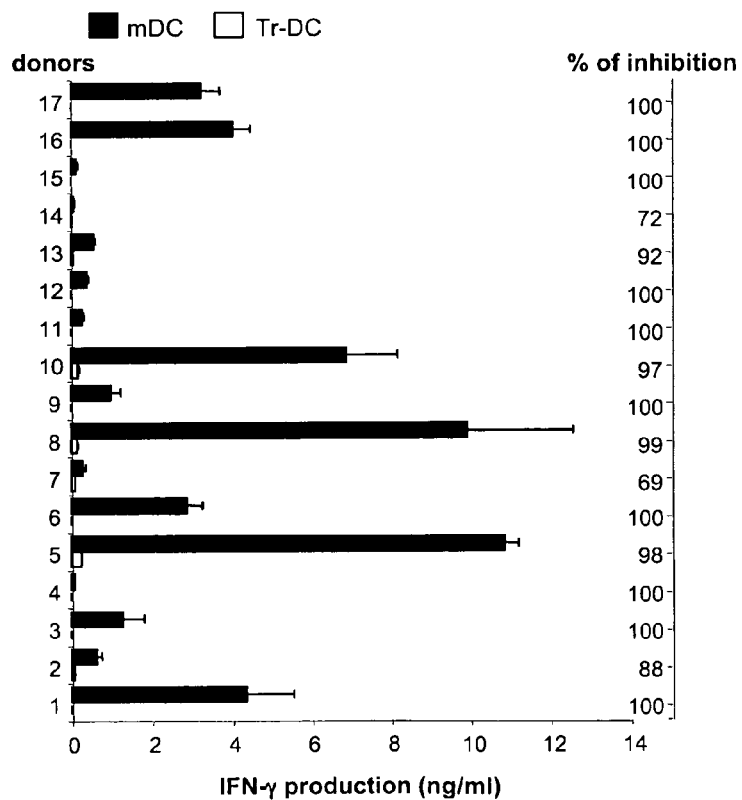

FIG. 12. Lack of stimulation capacity of Tr-DC. PBMC were cultured with allogeneic cells differentiated with IL-10 (Tr-DC) and mature DC (mDC) at ratio 1:10. A. Proliferate responses were evaluated 4 days after culture by [$^3$H]-thymidine incorporation for an additional 16 h B. In parallel, supernatants were collected after 48 hours and analyzed by ELISA to determine levels of IFN-γ. Numbers represent the % of inhibition of proliferation compared to that obtained with mDC.

Figure 13:
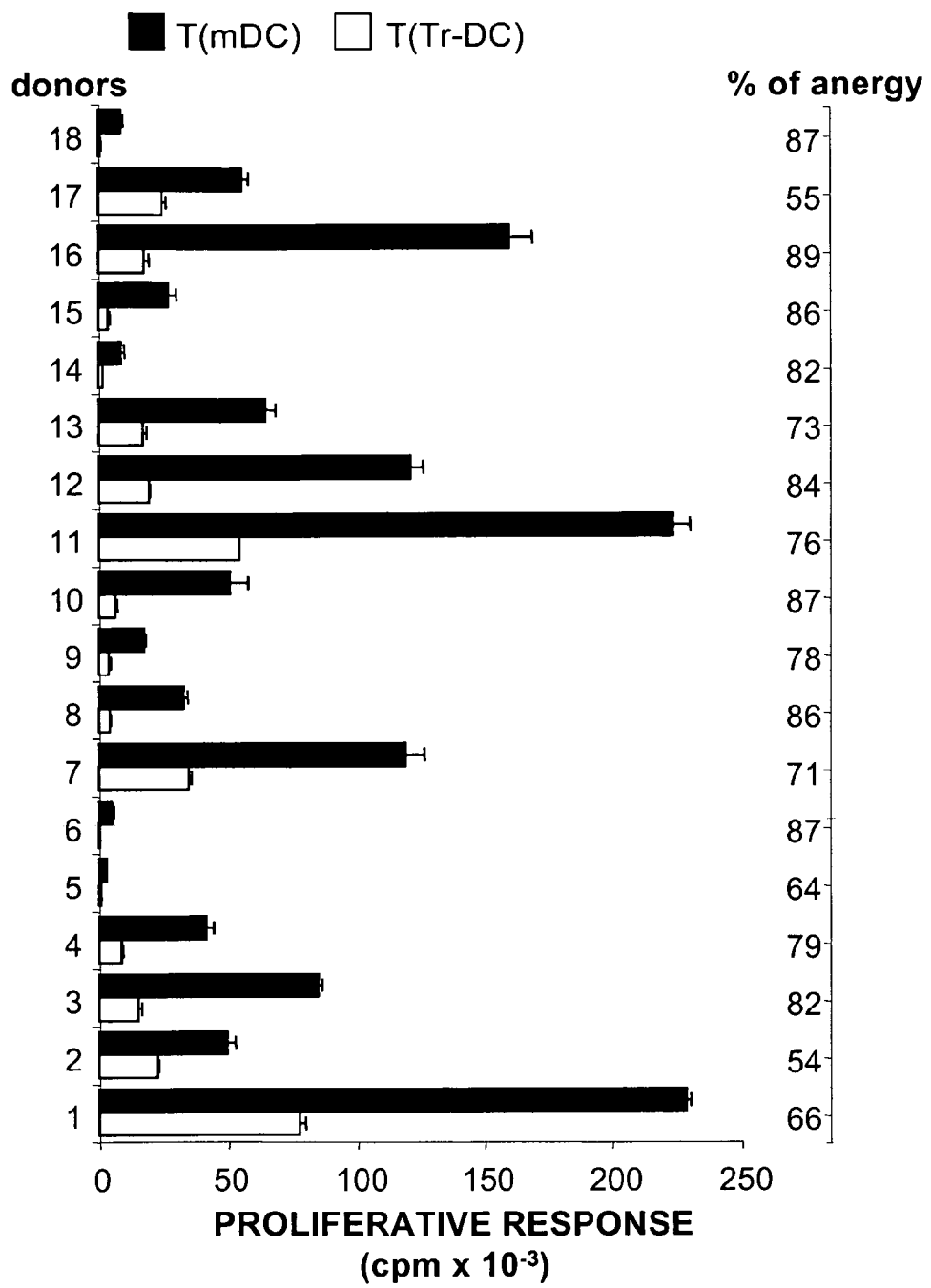

FIG. 13. Tr-DC induce anergic T cell. Total PBMC were stimulated with allogeneic Tr-DC [T(Tr-DC)] and mature DC [T(mDC)] at 1:10 ratio for ten days. After culture, T-cell lines were tested for their ability to proliferate in response to mature allogeneic DC. Proliferative responses were evaluated after 2 days of culture by [$^3$H]-thymidine incorporation for an additional 16 h. Numbers represent the % of anergy compared to mDC.

Figure 14:
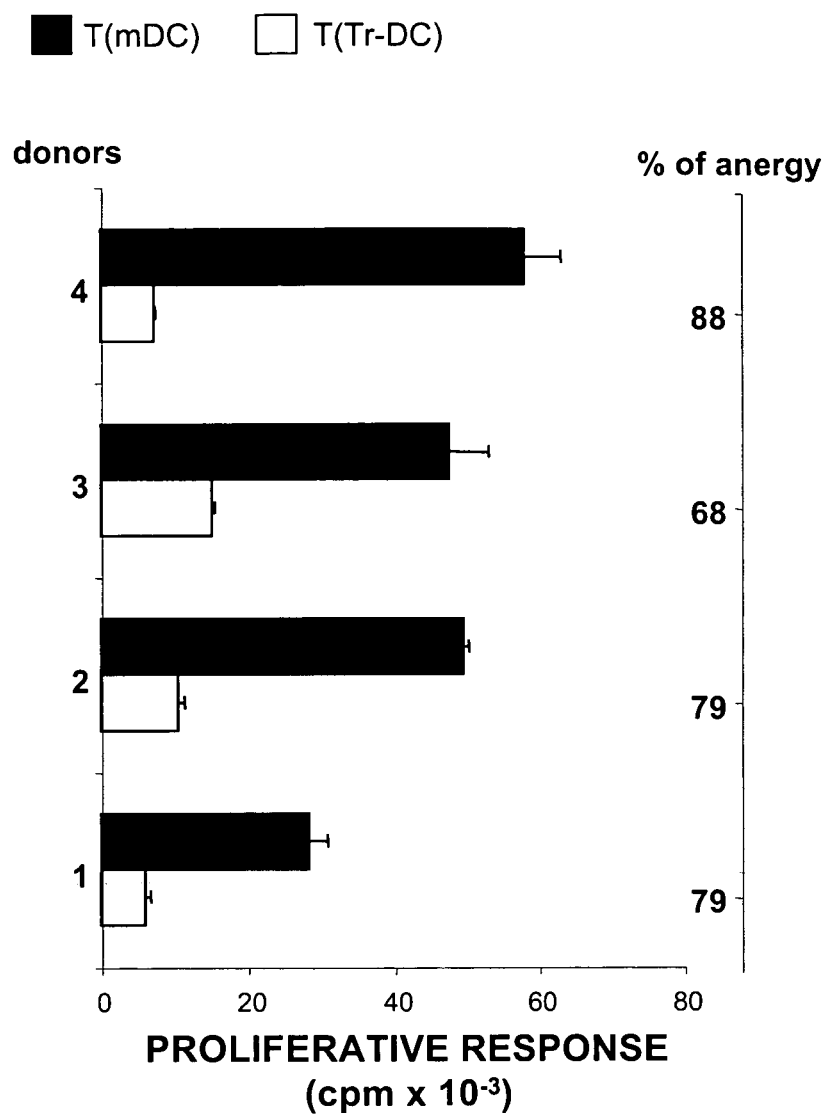

FIG. 14. Tr-DC induce anergic T cells in haplo-identical pairs. Total PBMC were stimulated with haplo-identical Tr-DC [T (Tr-DC)] or mature DC [T(mDC)] at 1:10 ratio for ten days. After culture, T-cell lines were tested for their ability to proliferate in response to mature allogeneic DC. Proliferative responses were evaluated by thymidine incorporation after 2 days of culture by [$^3$H]-thymidine incorporation for an additional 16 h. Numbers represent the % of anergy compared to mDC.

Figure 15:
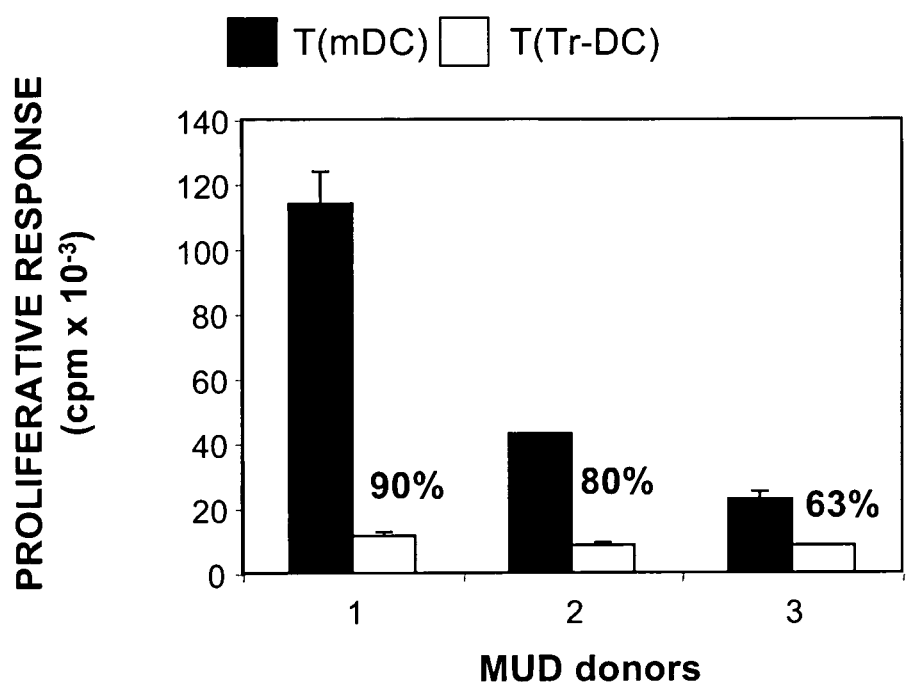

FIG. 15. Tr-DC induce anergic T cells in HLA-matched un-related (MUD) pairs. PBMC were stimulated with Tr-DC [T(Tr-DC)] or mature DC [T(mDC)] at 1:10 ratio for ten days. After culture, T-cell lines were tested for their ability to proliferate in response to mature allogeneic DC. Proliferative responses were evaluated by thymidine incorporation after 2 days of culture by [$^3$H]-thymidine incorporation for an additional 16 h. Numbers represent the % of anergy compared to mDC.

Figure 16:
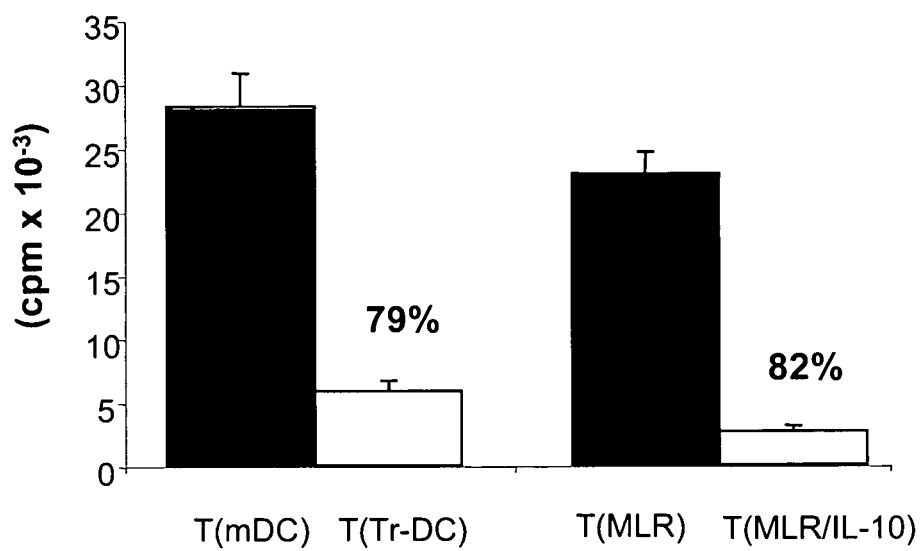

FIG. 16. Tr-DC are equivalent to exogenous IL-10 to generate anergic T cells in haplo-identical pairs. Total PBMC were stimulated with Tr-DC [T(Tr-DC)] or mature DC [T(mDC)] at 10:1 ratio or with CD3-depleted cells in the absence [T(MLR)] or in the presence of exogenous IL-10 [T(MLR/IL-10)] at 1:1 ratio for ten days. After culture, T-cell lines were tested for their ability to proliferate in response to mature allogeneic DC. Proliferative responses were evaluated after 2 days of culture by [$^3$H]-thymidine incorporation for an additional 16 h. Numbers represent the % of anergy compared to mDC.

Figure 17:
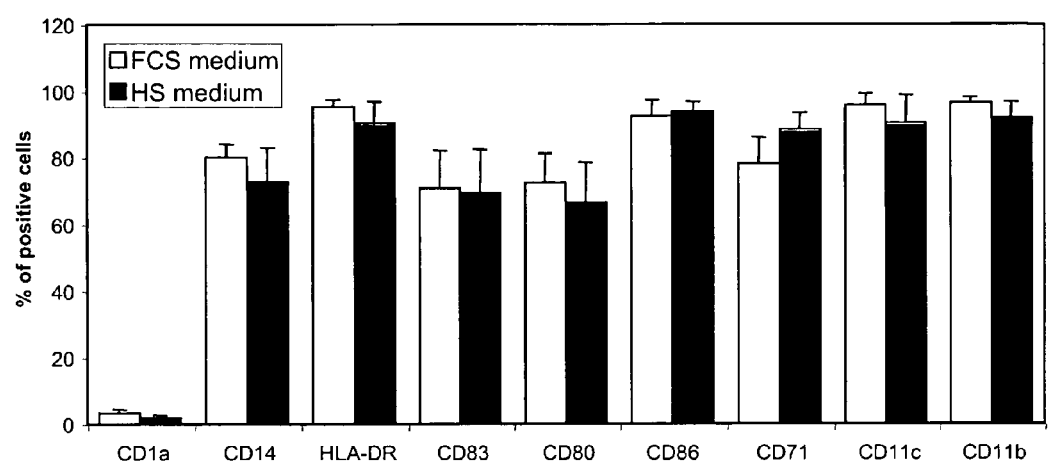
Figure 17:
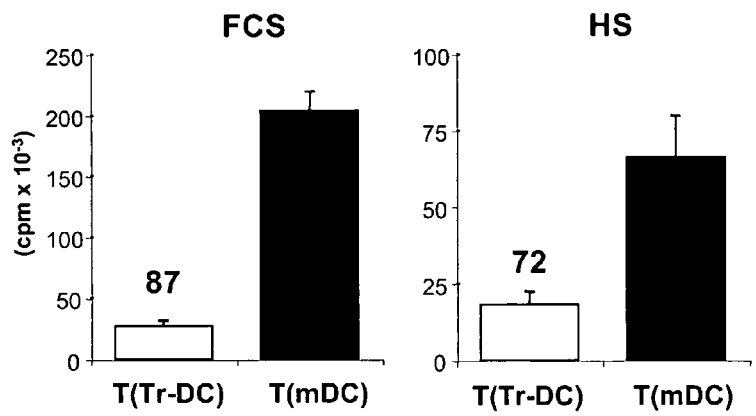

FIG. 17. Comparison between Tr-DC generated in medium containing FBS or HS. Monocyte-derived DC were differentiated in IL-4 and GM-CSF in the presence of IL-10 (Tr-DC) for 7 days in medium containing FBS or HS. A. Expression levels of CD1a, CD14, CD83, HLA-DR, CD83, CD80, CD86, CD11c and CD11b were evaluated by FACS analysis. B. Total PBMC were stimulated with Tr-DC [T(Tr-DC)] or mature DC [T(mDC)] generated in medium containing FCS or HS at 1:10 ratio for ten days. After culture, T-cell lines were tested for their ability to proliferate in response to mature allogeneic DC. Proliferative responses were evaluated after 2 days of culture by [$^3$H]-thymidine incorporation for an additional 16 h. Numbers represent the % of anergy compared to mDC.

Figure 18:
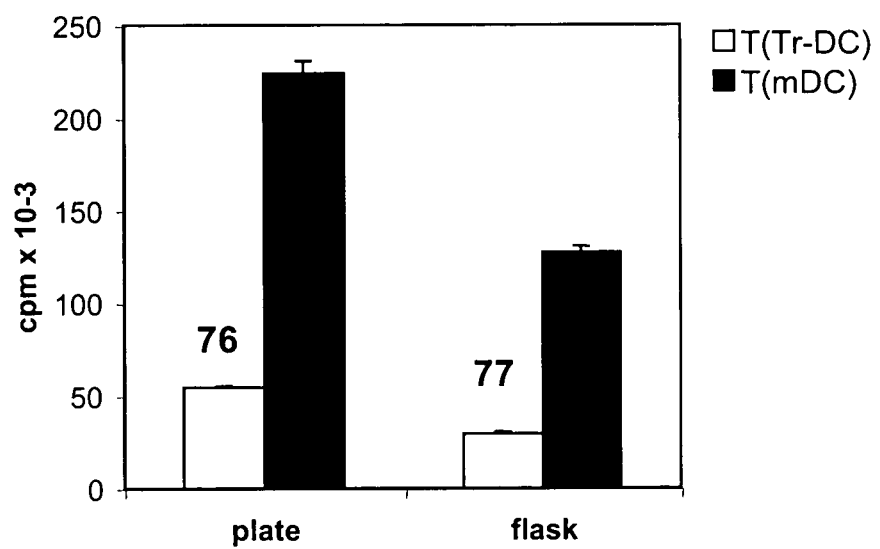

FIG. 18. Comparison between Tr-DC generated in flask and plate. Monocyte-derived DC were differentiated in IL-4 and GM-CSF in the presence of IL-10 (Tr-DC) for 7 days in flask or plate. Total PBMC were stimulated with with Tr-DC [T(Tr-DC)] or mature DC [T(mDC)] at 1:10 ratio for ten days. After culture, T-cell lines were tested for their ability to proliferate in response to mature allogeneic DC. Proliferative responses were evaluated after 2 days of culture by [$^3$H]-thymidine incorporation for an additional 16 h. Numbers represent the % of anergy compared to mDC.

Figure 19:
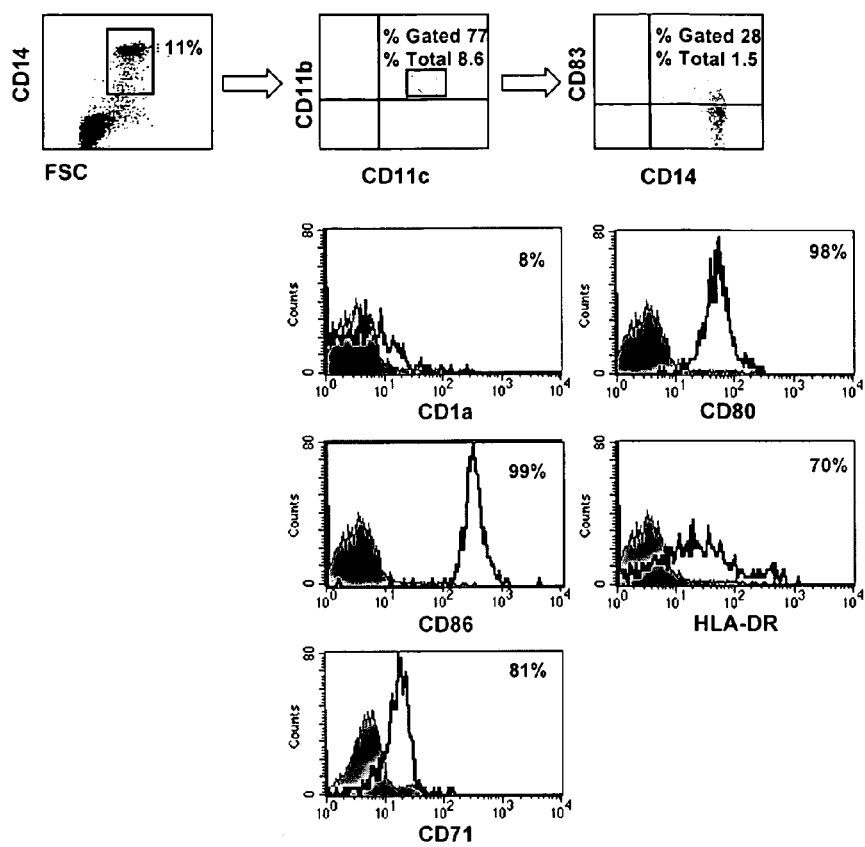
Figure 19:
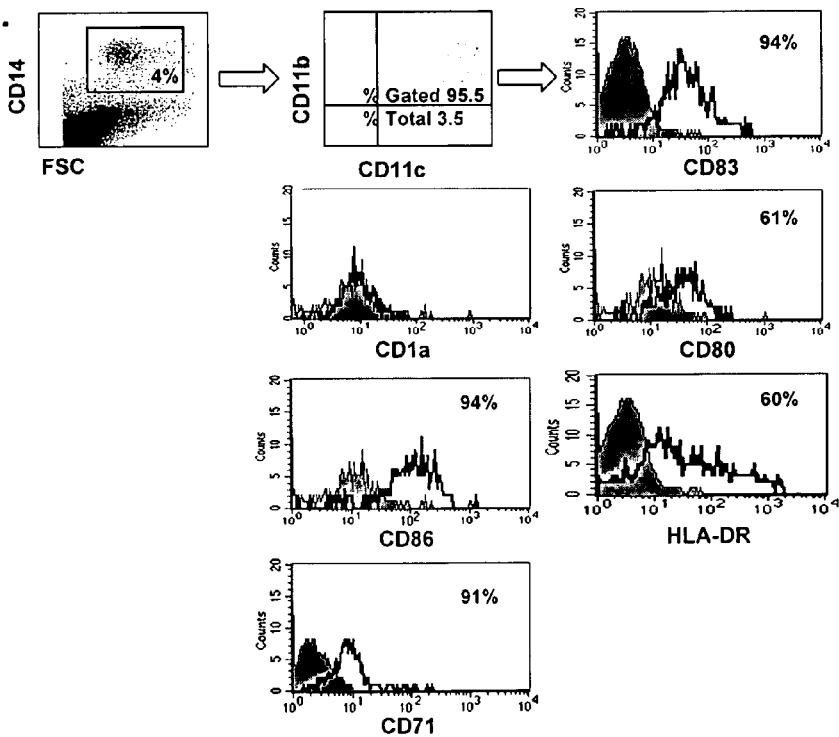

FIG. 19. Tr-DC are present in peripheral blood and human spleen. Expression levels of CD11c, CD11b, CD14, CD1a, CD80, CD83, CD86, CD71, and HLA-DR in peripheral blood (A), and in human spleens (B) were evaluated by FACS analysis. Analyses were performed on CD11b+CD11c+ gated cells. Filled histograms represent staining with the isotype-matched control mAbs. A representative donor out of six (A) and four (B) independent donors analyzed is presented. Percentages of CD11c+CD11b+ cells expressing the indicated markers are indicated.

Figure 20:
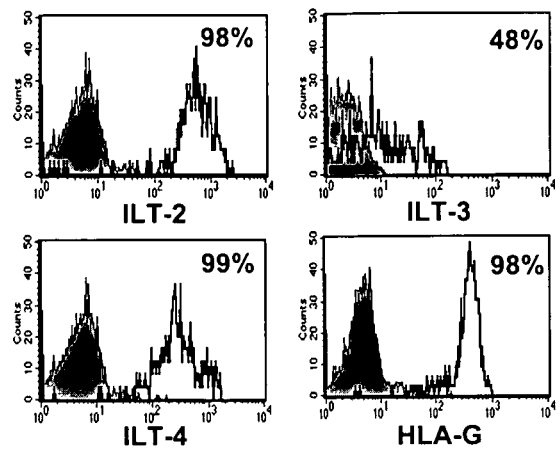
Figure 20:
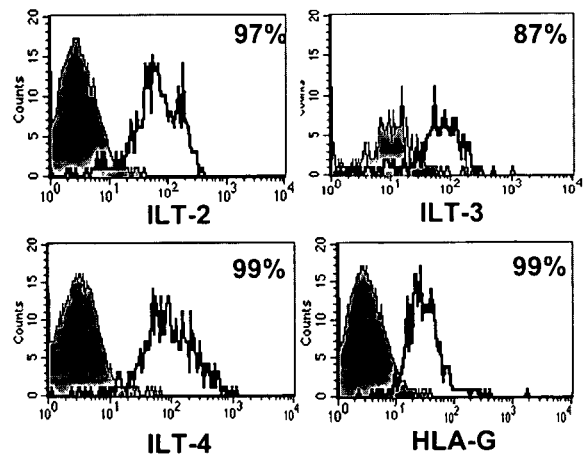

FIG. 20. Tr-DC present in peripheral blood and human spleens express the tolerogenic markers ILT-2, ILT-3, ILT-4, and HLA-G. Freshly isolated cells from peripheral blood (A) and human spleens (B) were analyzed by flow cytometry to determine levels of expression of ILT-2, ILT-3, ILT-4, and HLA-G. Analyses were performed on CD11b+CD11c+ gated cells. Filled histograms represent staining with the appropriate control mAbs. Data from one out of six (A), and four (B) independent donors analyzed are presented. Percentages of CD11c+CD11b+ cells expressing the indicated markers are indicated.

Figure 21:
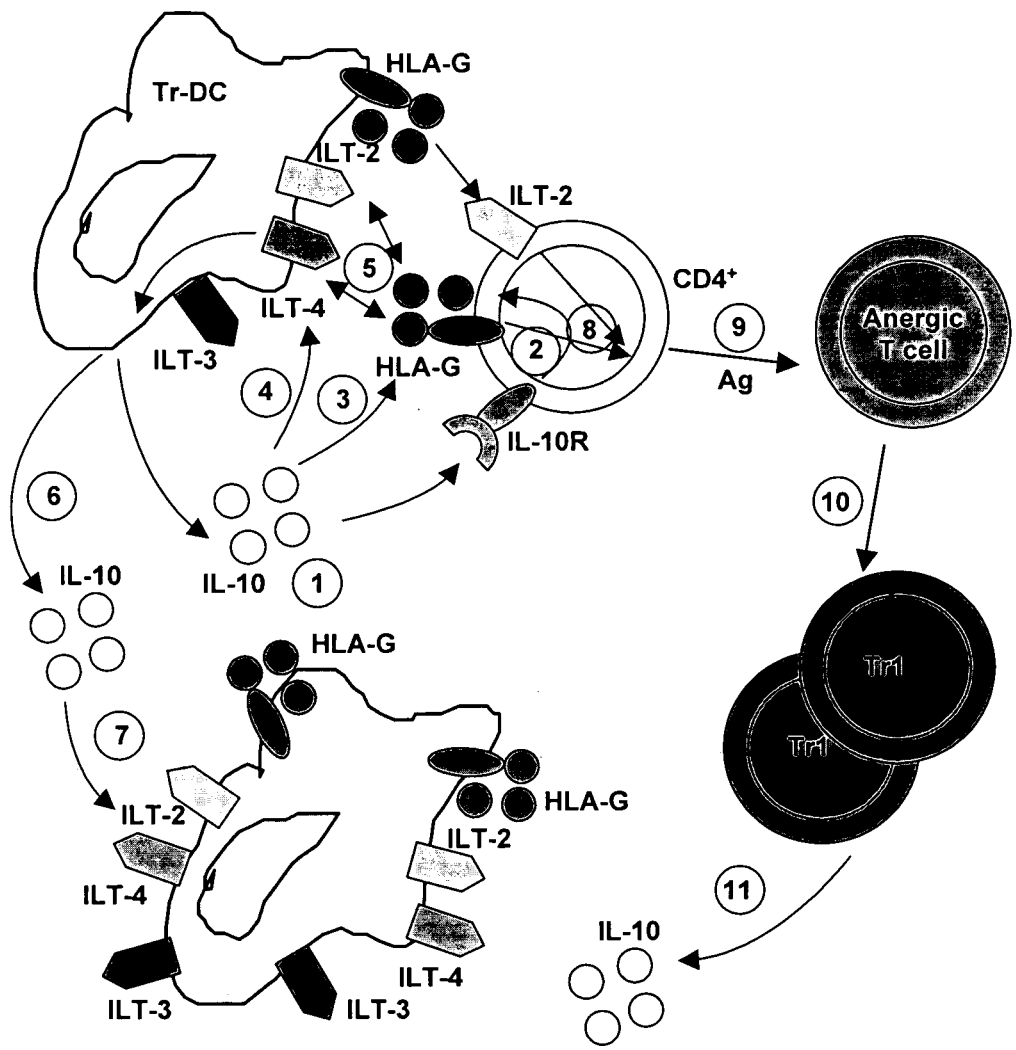

FIG. 21. Tr1 cells induction via the IL-10-dependent ILT-4/HLA-G pathway. Tr-DC secrete high levels of IL-10 (1). During T-cell priming, IL-10 produced by Tr-DC inhibits T cell proliferation (2) and promotes the up-regulation of HLA-G on allogeneic CD4+ T cells (3). IL-10 up-regulates ILT-2, ILT-3, ILT-4, and HLA-G on DC (4). HLA-G express on T cells interacts with ILT-4 on Tr-DC (5) and enhances IL-10 secretion (6). Tr-DC-derived IL-10 promotes de novo differentiation of tolerogenic DC by inducing ILT-2, ILT-3, ILT-4, and HLA-G expression (7). Concomitantly, interaction between ILT-2/ILT-4 on TR-DC and HLA-G on T cells, and HLA-G on Tr-DC and ILT-2 on T cells provides negative signals to T cells with further inhibition of their proliferation and cytokine production (8). This effect promotes T-cell anergy when T cells are re-challenged with the same Ag (9) and Tr1 cell differentiation (10). Tr1 cells secrete IL-10, which contributes to amplify this tolerogenic circuit (11).

Figure 22:
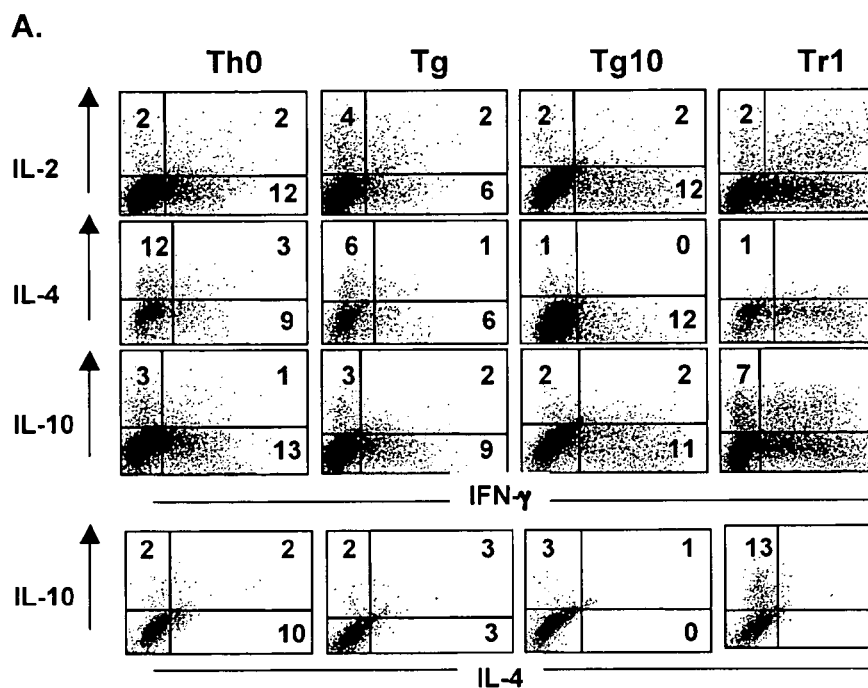
Figure 22:
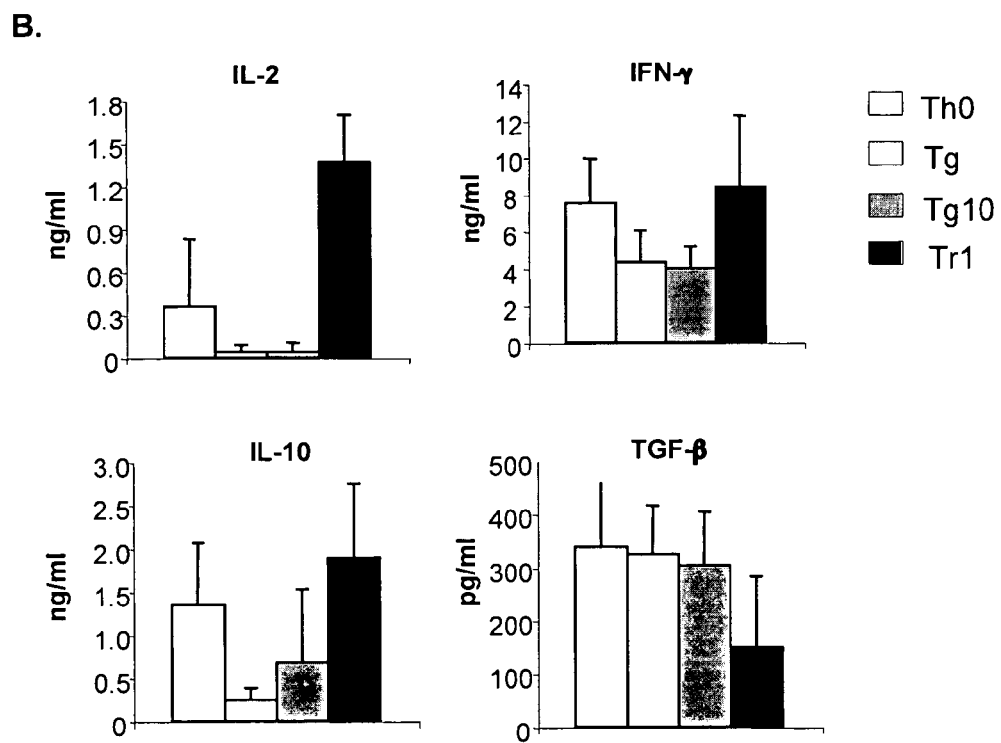

FIG. 22. Cytokine production profile of T cell lines differentiated in the presence of soluble HLA-G. Naïve CD4+ T cells were activated by anti-CD3 mAbs cross-linked on CD32+CD80+CD58+ L cells in the presence of exogenous IL-2 (Th0), soluble HLA-G1 (30 ng/ml) (Tg), soluble HLA-G1 (30 ng/ml) and exogenous IL-10 (10 ng/ml) (Tg10), or exogenous IL-10 (10 ng/ml) and IFN-α (5 ng/ml) (Tr1). A. Following two rounds of identical stimulation T cells were restimulated with immobilized anti-CD3 mAb (1 μg/ml) and TPA (10 ng/ml), and cytokine production was determine by intracytoplasmic staining. Percentages set according to the isotype-matched controls (not shown), are presented. One representative experiment out of six independent experiments is shown. B. Following two rounds of identical stimulation T cells were restimulated with coated anti-CD3 mAb (1 µg/ml) and soluble anti-CD28 (10 µg/ml). Culture supernatants were collected after 24 h, 48 h, and 72 h. IL-2 (24 h), IFN-γ, IL-10, and TGF-β (48 h) levels were determined by ELISA. Mean levels of cytokines collected in 5 experiments, ±StD are shown.

Figure 23:
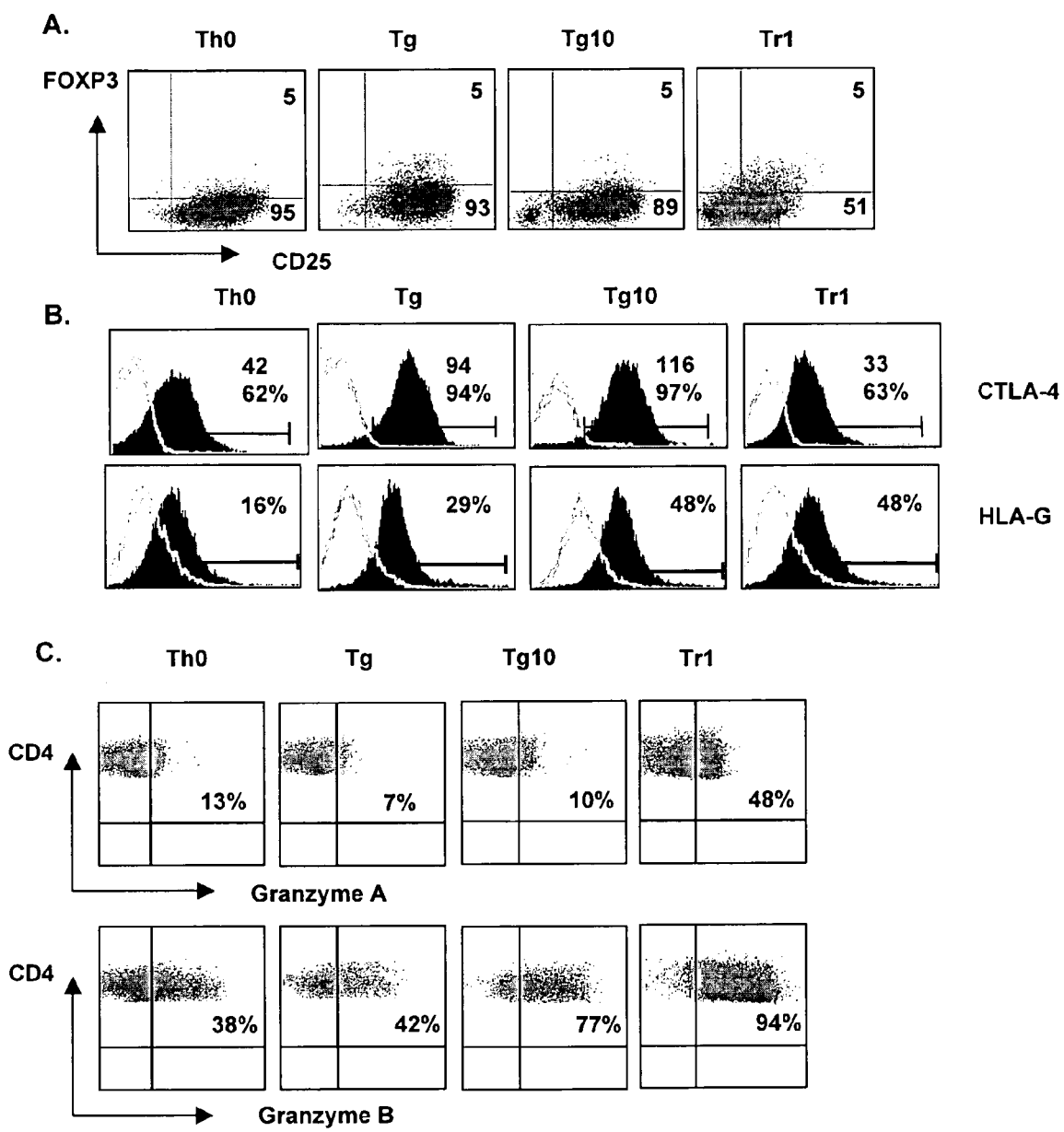

FIG. 23. Phenotype of T cell lines differentiated in the presence of soluble HLA-G. Naïve CD4+ T cells were activated by anti-CD3 mAbs cross-linked on CD32+CD80+CD58+ L cells in the presence of exogenous IL-2 (Th0), soluble HLA-G1 (30 ng/ml) (Tg), soluble HLA-G1 (30 ng/ml) and exogenous IL-10 (10 ng/ml) (Tg10), or exogenous IL-10 (10 ng/ml) and IFN-α (5 ng/ml) (Tr1). Following two rounds of identical stimulation T cells were analyzed for the expression of the indicated markers. The MFI (upper number) and the percentages (lower number) of positive cells, set according to the isotype-matched controls (not shown), are presented. Results from one representative experiment out of three (A), four (B), and six (C) performed are presented.

Figure 24:
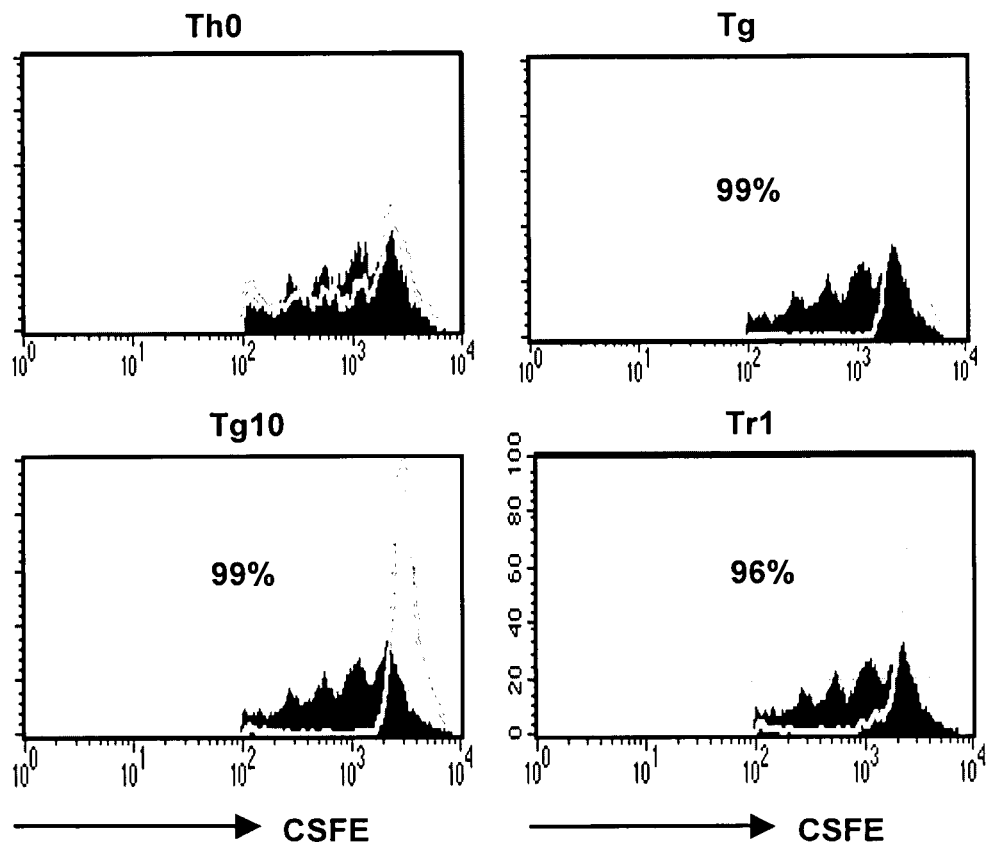

FIG. 24. T cells differentiated with soluble HLA-G alone or in combination with IL-10 are suppressor cells. Naïve CD4+ T cells were activated by anti-CD3 mAbs cross-linked on CD32+CD80+CD58+ L cells in the presence of exogenous IL-2 (Th0), soluble HLA-G1 (30 ng/ml) (Tg), soluble HLA-G1 (30 ng/ml) and exogenous IL-10 (10 ng/ml) (Tg10), or exogenous IL-10 (10 ng/ml) and IFN-α (5 ng/ml) (Tr1). Following two rounds of identical stimulation T cells were tested for their ability to suppress proliferation CSFE-labeled autologous CD4+CD45RO+ T cells were stimulated with coated anti-CD3 mAb (10 µg/ml) and soluble anti-CD28 (1 µg/ml) in the presence (open histograms) or absence (closed histograms) of Th0, Tg, Tg10, and Tr1 at 1:1 ratio. After 6 days were analyzed by flow cytometry. Percentages of suppression are presented. One representative experiment out of four independent experiments.

MATERIAL AND METHODS

Cell Preparations

Human peripheral blood was obtained from healthy donors in accordance with local ethical committee approval. Peripheral blood mononuclear cells (PBMC) were separated by density gradient centrifugation over Lymphoprep (Nycomed Amersham). Human spleens were obtained from cadaveric multiorgan donors through the North Italian Transplant Organization. Spleen cells were obtained by mechanical disruption of the organ followed by density gradient centrifugation over Lymphoprep.

Differentiation of DC

CD14+ monocytes were isolated as the adherent fraction following incubation for 1 hour in RPMI 1640 (Biowhittaker) supplemented with 10% FCS (Biowhittaker), 100 U/ml penicillin/streptomycin (Bristol-Myers Squibb), and 50 µM 2 mercaptoethanol (BioRad) (DC medium) at 37° C. Following extensive washing, adherent monocytes were cultured in 10 ng/ml rhIL-4 (R&D Systems) and 100 ng/ml rhGM-CSF (R&D Systems) in DC medium alone (obtained cells are named immature DC, iDC) or in the presence of 10 ng/ml of rhIL-10 (BD, Bioscience, obtained cells are named Tr-DC) for 7 days. Alternatively, adherent monocytes were cultured in 10 ng/ml rhIL-4 (R&D Systems) and 100 ng/ml rhGM-CSF (R&D Systems) in DC medium alone for 5 days and matured with 1 µg/ml of LPS (Sigma Aldrich, obtained cells are named mature DC, mDC) for additional 2 days. At day 7, immature DC (iDC), DC generated in the presence of IL-10 (Tr-DC), and mature DC (mDC) were collected, irradiated (6000 RADS) and used to stimulate naïve CD4+ T cells or PBMC, therefore obtaining T(iDC), T(Tr-DC) and T(mDC) cell lines. The purity and maturation state of DC were routinely checked by flow cytometric analysis to determine expression of CD1a, CD14, CD83 and HLA-DR. In some experiments iDC, Tr-DC, and mDC were either left un-stimulated or activated with 50 ng/ml of rhIFN-γ (R&D Systems) and 200 ng/ml of LPS (Sigma) for additional 2 days. In some experiments iDC, Tr-DC, and mDC were also tested for levels of expression of CD11c, CD11b, CD71, CD80, CD83, CD86, ILT-2, (BD Biosciences), ILT-3 (Coulter Immunotech) and ILT-4 (kind gifts from Marco Colonna), ICOS-L (eBioscience), and HLA-G (Exbion).

Purification of T Cells

CD4+ T cells were purified from PBMC by negative selection using the CD4+ T cell Isolation kit (Miltenyi Biotech), according to the manufacture's instructions. A portion of the resulting CD4+ T cells was cryopreserved for later use, and the remainders were depleted of CD45RO+ cells using anti-CD45RO-coupled magnetic beads and LD negative selection columns (Miltenyi Biotech). In the purified cells the proportion of CD4+CD45RO−CD45RA+ was consistently greater than 90%.

T Cell Differentiation Using DC.

$1 \times 10^5$ DC (iDC, Tr-DC, and mDC) were cultured with $1 \times 10^6$ allogeneic naïve CD4+CD45RO− T cells in 1 ml of X-vivo 15 medium (Biowhittaker), supplemented with 5% pooled AB human serum (Biowhittaker), and 100 U/ml penicillin/streptomycin (Bristol-Myers Squibb). After 6 or 7 days, rhIL-2 (40 U/ml) (Chiron) was added, and cells were expanded for an additional 7 days. Fourteen days after initiation of the culture, T cells were collected, washed and analyzed for their proliferative capacity and cytokine secretion profile. In parallel, a proportion of T cell lines was restimulated with immature, Tr-DC or mature DC from the same allogeneic donor used in the primary culture. After 3 days, rhIL-2 was added. One week after initiation of the second stimulation, T cells were collected and analyzed for their proliferative capacity and cytokine secretion profile. Alternatively, $1 \times 10^5$ DC (Tr-DC and mDC) were cultured with $1 \times 10^6$ allogeneic PBMC cells in 1 ml. HLA-mismatched donor pairs, HLA-haploidentical pairs or HLA-matched un-related (MUD) pairs were tested. At day seven half of the medium, with or without cytokine, was replaced with fresh one. Ten days after initiation of the culture, T cells were collected, washed and analyzed for their proliferative capacity and cytokine secretion profile. Naïve CD4+ T cells or PBMC stimulated with immature DC are referred to as T(iDC) and those stimulated with Tr-DC as T(Tr-DC) and those stimulated with mature DC as T(mDC). In some experiments, neutralizing anti-IL-10R (3F9, 30 mg/ml, BD Pharmingen), anti-ILT-4 (10 µg/ml, kind gift from Marco Colonna) or anti-HLA-G (10 µg/ml 87 G, Exbion) mAbs were added at the initiation of each round of stimulation and each time the cells were split. Cultures with immature DC and Tr-DC typically resulted in 8-10-fold reduction in T-cell expansion compared to cultures stimulated with mature DC. This reduced recovery was not due to increased cell death as measured by annexin V staining (data not shown).

Alternatively, $5 \times 10^5$ CD3-depleted PBMC were co-culture with the same number of allogeneic PBMC in a final volume of 1 ml, in the presence (CD3-APC+IL-10) or absence (CD3-APC) of exogenous IL-10 (10 ng/ml). At day seven half of the medium, with or without cytokine, was replaced with fresh one. At day ten cells were collected, washed, and analyzed for their proliferative response in response of newly prepared CD3-depleted cells. PBMC stimulated with (CD3-APC) are referred as T(MLR) and with (CD3-APC+IL-10) as T(MLR/IL-10).

T Cell Differentiation Using L Cells.

Murine L cells transfectants expressing hCD32 (FCgRII), hCD58 (LFA-3), and hCD80 (48) were cultured in RPMI 1640 (Biowhittaker) supplemented with 10% FCS (Biowhittaker), 100 U/ml penicillin/streptomycin (Bristol-Myers Squibb). L cells were detached by incubation with trypsin-EDTA (Life-Technologies) and irradiated (700 rad) by x-ray source. Following washing, cells were plated in 24-well plates at initial density of $4 \times 10^5$ cells/ml in 500 μl volume of X-vivo 15 medium (Biowhittaker), supplemented with 5% pooled AB human serum (Biowhittaker), and 100 U/ml penicillin/streptomycin (Bristol-Myers Squibb), and 100 ng/ml of anti-CD3 (OKT3 Jansen-Cilag, Raritan, N.J.). After the L cells has adhered, 500 μl of naïve CD4+ T cells were added at an initial density of $4 \times 105$ cells/ml in complete medium.

All the experiments were conducted in the presence of recombinant human IL-2 (100 U/ml) (Chiron) and human recombinant IL-15 (1 ng/ml) (R&D) (obtained cells are named Th0 cells). In addition, the following soluble factors were added as indicated: rhIL-10 (10 ng/ml) (BD, Bioscience), rh-IFN-α (5 ng/ml) (R&D) (obtained cells are named Tr1 cells), soluble HLA-G1 (30 ng/ml) alone (obtained cells are named Tg) or in combination with rhIL-10 (10 ng/ml) (obtained cells are named Tg10). T cells were split as necessary, IL-2 and IL-15 were replenished in all cultures. At day 7, T cells were collected, washed, counted, and restimulated under identical conditions for an additional 7 days. At day 14 of in vitro culture, cells were collected, washed, counted, and analyzed for their profile of cytokine production and proliferative capacity. Soluble HLA-G1 was collected from culture supernatants of transfected line 0.221-G (34).

Proliferation and Suppression of T Cells.

To analyze the proliferative capacity of T(iDC), T(Tr-DC), or T(mDC) in response to allogeneic APC, T cells were thawed and stimulated with either allogeneic mDC (10:1, T:DC) or monocytes (CD3-depleted PBMCs, irradiated 6000 RADS) (1:1, T:monocytes) in a final volume of 200 μl of medium. To test for the capacity of T(iDC), T(Tr-DC), or T(mDC) cells to suppress proliferation and/or cytokine production, autologous CD4$^+$ T cells were thawed and stimulated with allogeneic mDC (10:1, T:DC) in the absence or in the presence of T(iDC), T(Tr-DC), or T(mDC) cells (1:1 ratio) in a final volume of 200 μl of complete medium in 96 well round-bottom plates. In some cultures, autologous CD4$^+$ T cells were stimulated with allogeneic monocytes (CD3-depleted PBMCs, irradiated 6000 RADS) (1:1, T:monocytes in the absence or in the presence of T(Tr-DC) cells (1:1 ratio) and neutralizing anti-IL-10R (30 μg/ml, 3F9, BD Bioscience) and/or anti-TGF-β (50 μg/ml, 1D11, R&D systems) mAbs were added. After the indicated time, cells were either pulsed for 16 hours with 1 μCi/well $^3$H-thymidine or supernatants were collected for analysis of IFN-γ production.

To test for the suppressive capacity of T cell lines via flow cytometry, naïve CD4$^+$ T cells were labeled with CFSE (Molecular Probes) and stimulated with coated anti-CD3 mAb (10 μg/ml) and soluble anti-CD28 (1 μg/ml) in the presence or absence (closed histograms) of Th0, Tg, Tg10, and Tr1 at 1:1 ratio. After 6 days, proliferation of the CFSE-labeled naïve T cells was determined by flow cytometric analysis.

Cytokine Determination: Intracytoplasmic Staining and ELISA.

To measure IFN-γ IL-2, IL-10, and TGF-β production, culture supernatants were harvested 48, 72 and 96 hours after culture and levels of IFN-γ were determined by capture ELISA according to the manufacturer's instructions (BD Biosciences). To measure IL-10 and IL-12 produced by iDC, Tr-DC, and mDC, cells were left un-stimulated or activated with 50 ng/ml of rhIFN-γ (R&D Systems) and 200 ng/ml of LPS (Sigma) for additional 2 days. Supernatants were harvested after 48 hours. Levels of IL-10 and IL-12 were determined by capture ELISA according to the manufacturer's instructions (BD Biosciences). The limits of detection were as follows: IFN-γ: 60 pg/ml; IL-10: 20 pg/ml; IL-12: 20 pg/ml.

Intracellular cytokines were detected by flow cytometry as previously described (47). Briefly, T cells ($1 \times 10^6$/ml) were stimulated with immobilized anti-CD3 (1 μg/ml; OKT3, Jansen-Cilag, Raritan, N.J.) and TPA (10 ng/ml; Sigma) in complete medium. Prior to the culture, the plates were centrifuged for 5 min at 800×g. Three hours after activation, brefeldin A (10 μg/ml; Sigma) was added. Six hours after activation, T cells were collected, washed in PBS, and fixed with 2% formaldehyde. After fixation, T cells were permeabilized by incubation in PBS supplemented with 2% FCS and 0.5% saponin (Sigma). Permeabilized T cells were incubated with anti-hIL-2, or anti-hIL-10, and FITC-coupled anti-hIFN-γ or anti-hIL-4 mAbs. All mAbs were obtained from PharMingen. After washing, cells were analyzed using a FACScan flow cytometer (BD Biosciences, Mountain View, Calif.), and data were analyzed with CellQuest software (BD Biosciences). Quadrant markers were set accordingly to isotype-matched controls (data not shown).

Quantitative PCR.

Total RNA was extracted with Eurozol (Euroclone, Celbio), and cDNA was synthesized using the high capacity cDNA archive kit (Applied Biosystems). Levels of IL-10, IL-12 and HPRT mRNA were quantitated using Assay on Demand real-time PCR kits (Applied Biosystems) with TaqMan Master Mix (Applied Biosystem). Samples were run in duplicate, and relative expression of IL-10 and IL-12 was determined by normalizing to HPRT expression in each set of samples to calculate fold-change in value.

FACS Analysis.

Anti-CD4, -CD25, -CD122, and -CD132, directly coupled with FITC and PE were purchased from BD. Expression of IL-15Rα was determined with biotinylated anti-IL-15Rα mAb (BD Bioscience) followed by streptavidin PE-conjugated (BD Bioscience). Expression of FOXP3 was determined by intracellular staining with FITC conjugated anti-FOXP3 mAb (clone PCH101, e-bioscience), following the manufacturer's instructions. Expression of CTLA-4, Granzyme A, and Granzyme B were determined by intracellular staining. Briefly, T cells were collected, washed in PBS, and fixed with 2% formaldehyde. After fixation, T cells were permeabilized by incubation in PBS supplemented with 2% FCS and 0.5% saponin (Sigma). Permeabilized T cells were incubated with PE-labeled anti-CTLA-4 (BD Bioscience), anti-granzyme A (BD Bioscience), or anti-granzyme B (Caltag). After washing, cells were analyzed using a FACScan flow cytometer (BD Biosciences, Mountain View, Calif.), and data were analyzed with CellQuest software (BD Biosciences).

Statistical Analysis.

All analysis for statistically significant differences were performed with the student's paired t test. P values less than 0.05 were considered significant. All cultures were performed in triplicate and error bars represent the SD.

Results

IL-10 Prevents Down-Regulation of CD14 and Up-Regulation of CD1a on DC.

To determine the effect of exogenous IL-10 on the differentiation of dendritic cells (DC), DC were differentiated from CD14+ monocytes in the presence of IL-4 and GM-CSF for 7 days with exogenous IL-10 (Tr-DC), alternatively cells were differentiated with IL-4 and GM-CSF for 5 days in the absence of IL-10 and then left unstimulated (immature DC, iDC) or activated with LPS (mature DC, mDC) for additional 2 days. The authors observed that addition of exogenous IL-10 profoundly modified the morphology of the resulting cells. DC generated in the presence of exogenous IL-10 (Tr-DC) were large, granular and displayed few cytoplasmic expansions compared to immature and mature DC (FIG. 1A). IL-10 prevented the down-regulation of CD14 and the up-regulation of CD1a as observed in immature and mature DC (FIG. 1B). Further phenotypic characterization of Tr-DC revealed an expression of CD83, CD80, and CD86 similar to that observed in mature DC. CD11c, CD11b, and CD71 were similarly expressed by Tr-DC, immature, and mature DC (FIG. 1B).

The specific dendritic cell markers expressed by Tr-DC are summarized in Table I.

TABLE I

Comparison of specific dendritic cell markers expressed by immature, mature and Tr1 dendritic cells.

| Dendritic cell type/specific markers | iDC | mDC | tolerogenic cells (Tr-DC) identified by the present method |
|---|---|---|---|
| CD14 | − | − | + |
| CD11c | + | + | + |
| CD11b | + | + | + |
| CD83 | − | + | + |
| CD80 | − | + | + |
| CD86 | +/− | + | + |
| CD71 | + | + | + |
| HLA-DR | + | + | + |
| CD1a | + | + | − |

Tr-DC Secrete Higher Levels of IL-10 Compared to Immature DC.

Tr-DC secrete significantly higher amounts of IL-10 compared to iDC and mDC, whereas they secrete low amounts of IL-12, which are comparable to those produced by iDC (FIG. 1C). Interestingly, upon activation with LPS and IFN-γ Tr-DC and iDC produce equal amounts of IL-10, but, in contrast to iDC, Tr-DC do not secrete significant levels of IL-12 (FIG. 1D).

These results were paralleled by the analysis of the mRNA levels of both IL-10 and IL-12. IL-10 mRNA levels were significantly higher in Tr-DC compared to iDC, whereas the mRNA levels for IL-12 were comparable in the two cell types (FIG. 2A). Importantly, upon activation, Tr-DC displayed significantly higher amounts of mRNA for IL-10 compared to iDC. In addition, the mRNA level for IL-12 remains low (FIG. 2B).

These results indicated that Tr-DC are refractory to activation and maintain their ability to express and secrete IL-10 but not IL-12. All together these data clearly demonstrated that addition of exogenous IL-10 results in the differentiation of a novel subset of tolerogenic DC (Tr-DC), which are distinct from immature and mature DC.

Tr-DC Display Low Stimulatory Capacity.

Naïve CD4+ T cells stimulated with allogeneic Tr-DC display a significantly lower proliferative response with a reduction in proliferation of 85±17% (mean±SD, n=24), when compared to naïve CD4+ T cells primed with mDC (one representative experiment in FIG. 3A). As expected, iDC also poorly stimulated allogeneic naïve CD4+ T cells (a mean±SD reduction in proliferation of 65±22% (mean±SD, n=24), compared to proliferation induced by mDC). However, the stimulatory capacity of Tr-DC was significantly reduced compared to that of iDC (n=24, p=0.0008). Similarly, IFN-γ production by naïve CD4+ T cells stimulated with allogeneic Tr-DC was reduced when compared to production by naïve CD4+ T cells primed with mDC, and was significantly lower than that induced by iDC (a mean±SD reduction of 88±14% vs. 61±30% with Tr-DC and iDC, respectively, n=8, p=0.035) (one representative experiment in FIG. 3B). Importantly, Tr-DC activated with IFN-γ and LPS maintained their reduced stimulatory capacity as proliferation induced by activated Tr-DC was significantly reduced compared to that generated by activated iDC (a mean±SD reduction of 89±8% vs. 4±6% with Tr-DC and iDC, respectively, n=4, p<0.0001) (one representative experiment in FIG. 3C). Indeed, activated iDC acquired a mature phenotype and induced proliferation of allogeneic CD4+ T cells similar to that of mDC (FIG. 3C). These data show that upon activation Tr-DC maintain their low stimulatory capacity.

Tr-DC Induce T-Cell Anergy.

Tr-DC promote T-cell anergy, since naïve CD4+ T cells activated with Tr-DC, become unable to proliferate when restimulated with mDC from the same donor. After one round of stimulation, T cells generated with allogeneic Tr-DC [T(Tr-DC)] were already profoundly hypo-responsive to re-activation with mDC, whereas T cells stimulated with iDC [T(iDC)] were not. Reduction in Ag-induced proliferation of 82±14% and of 38±26% (mean±SD, n=8) was observed in T cells primed with Tr-DC and iDC, respectively, in comparison to T cells primed with mDC [T(mDC)] (one representative donor in FIG. 4A). Similar results were obtained when IFN-γ production by T cell lines re-challenged with mDC was measured (FIG. 3B). After two rounds of stimulation both T(iDC) and T(Tr-DC) cells were anergic and displayed an average reduction of proliferation of 72±12% (n=8) and 81±2% (n=8, not significant), respectively (FIG. 4C). Thus, hypo-responsiveness could be acquired by naïve CD4+ T cells stimulated with iDC only after repeated Ag stimulation (19, 20), conversely the authors show here that Tr-DC efficiently promote T-cell anergy following a single activation, indicating that Tr-DC are more powerful inducers of T cell anergy compared to iDC.

Tr-DC Induce the Differentiation of IL-10-Producing Tr1 Cells.

T cells obtained after one round of stimulation with Tr-DC [T(Tr-DC)] contained a significant proportion of IL-10-producing cells (average: 8%, range: 4-10%, n=9), and a low proportion of IL-4-producing cells (average: 4%, range: 0-8%). In these culture conditions, IL-2-producing cells were on average 7% (range: 2.3-12%), and IFN-γ-producing cells were on average 16% (range: 3-20%). Conversely, T cells differentiated with iDC or mDC contained more IFN-γ-producing cells (on average 23%, range: 12-35% with iDC, and on average 40%, range: 22-67% with mDC,) and low IL-10-producing cells (on average 2.6%, range: 0.2-4.5% with iDC, and on average 2.7%, range: 0-5.2% with mDC). IL-10-producing cells were significantly high in T(Tr-DC) cell lines compared to T(iDC) and T(mDC) cell lines (p=0.00004) (FIG. 5A and FIG. 6).

After two rounds of stimulation with Tr-DC the proportion of IL-10-producing cells increased (average: 12%, range: 9.7-13.2%, n=3) and the proportion of IL-2-producing cells (average: 3.6%, range: 2.8-4.4%) and IFN-γ-producing cells (average: 15.4%, range: 11.2-21.3%) decreased (FIG. 5B). T cells induced by Tr-DC after one or two rounds of stimulation, secrete similar amounts of TGF-β compared to cells generated with immature DC [T(iDC)], and lower amounts compared to cells generated with mature DC [T(mDC)] (FIG. 5C).

Phenotypic analysis of T(Tr-DC) cell lines revealed a percentage of CD25$^+$ FOXP3$^+$ cells similar to that observed in T(iDC) and T(mDC) cell lines (FIG. 7A). The percentage of T cells expressing CD122, CD132, IL-15Rα and CTLA-4 was comparable among the T cell lines generated with different DC, but T(Tr-DC) cells expressed higher levels of CTLA-4. Interestingly, the percentage of T(Tr-DC) cells expressing granzyme B was also higher compared to that observed in T(iDC) and T(mDC) cells, whereas the percentage of cells expressing granzyme A was comparable among the three T cell populations (FIG. 7B). In summary, the T cells induced by Tr-DC are IL-10$^{++}$, TGF-β$^+$, IL-4$^-$ and IFN-γ and IL-2 negative to low and are phenotypically similar to Tr1 cells.

Anergic T cells generated with Tr-DC suppress primary T-cell responses. Proliferation and IFN-γ production by naïve CD4$^+$ T cells stimulated with mDC (MLR) was significantly suppressed by the addition of T(Tr-DC) cells (FIGS. 8A and B). Proliferation of naïve CD4$^+$ T cells stimulated with mature DC had the kinetics of a primary response, peaking at day 4 of culture (FIG. 8C), whereas, as previously demonstrated (20), proliferation of T(mDC) restimulated with mDC peaked at day 2 and decrease at day 3 and 4, which is consistent with the kinetic of a secondary response (FIG. 8C). Interestingly, T(Tr-DC) cells acquired suppressive function after a single stimulation (FIGS. 8A and C), whereas addition of T(iDC) cells, obtained after one round of stimulation, to the primary MLR resulted in increased proliferation at day 2 and 3 (FIGS. 8A and C). These data were mirrored when we examined production of IFN-γ: addition of T(mDC) cells to the primary MLR resulted in an additive effect, whereas addition of T(Tr-DC) cells resulted in an almost complete suppression of IFN-γ production (FIGS. 8B and D). As expected, after two rounds of stimulation T cell lines generated with iDC (T(iDC) and Tr-DC T(Tr-DC) suppress naïve primary MLR (FIG. 8C). These findings indicate that Tr-DC potently promote the induction of anergic T cells with suppressive activity after single priming.

T cell lines generated with Tr-DC suppress primary MLR via an IL-10- and TGF-β mediated mechanism, since suppression was completely reversed by the addition of neutralizing anti-IL-10R and anti-TGF-β mAbs (FIGS. 9A and B). In addition, T(Tr-DC) cells do not require cell-cell contact for their suppressive activity since suppression of MLR was observed in experiments performed using transwell chambers (data not shown). Furthermore, T(Tr-DC) cells were anergic towards allo-Ags but preserved their ability to proliferate in response to nominal Ags, such as Tetanus Toxoid and *Candida Albicans* (data not shown).

Overall, these data indicate that T cells generated by Tr-DC are functionally equivalent to Tr1 cells. Differentiation of Tr1 cells with either iDC (20) or immuno-modulators, such as IL-10 alone (1) or in combination with IFN-α (47), or vitamin D$_3$ and dexamethasone (49), requires repetitive Ag stimulations. Conversely, the authors show that Tr-DC promote the differentiation of IL-10-producing Tr1 cells after a single stimulation. These findings are important for the prospective clinical application of Tr1 cells, since rapid and efficient ex-vivo differentiation combined with Ag-specificity are desired characteristics for cellular therapy with regulatory T cells.

Tr-DC promote Tr1 cell differentiation via IL-10, since naïve CD4$^+$ T cells stimulated with Tr-DC in the presence of neutralizing anti-IL-10R were not anergic (data not shown) and did not acquire suppressive activity (FIGS. 9C and D). These results indicate that IL-10 is required for the differentiation of Tr1 cells by Tr-DC and are in line with our previous study demonstrating that autocrine production of low amounts of IL-10 by iDC is a necessary component for induction of Tr1 cells after repetitive Ag stimulation (20).

Differentiation of Tr1 Cells by Tr-DC Requires ILT-4/HLA-G Pathway.

Tr-DC express significantly higher levels of immunoglobulin like-transcript (ILT)-2, ILT-3, ILT-4, and HLA-G, compared to iDC (FIGS. 10A and B). Interestingly, no differences in the expression of ICOS-L were observed between Tr-DC and iDC (FIGS. 10A and B). Several immuno-modulants such as IL-10 (29), IFN-α (50), and vitamin D$_3$ (51) have been reported to up-regulate ILT-3 and ILT-4 expression on DC. Interestingly, the same compounds have been shown to promote differentiation of regulatory T cells (47, 49). Furthermore, DC expressing ILT-4 or HLA-G are poor stimulators and promote the induction of anergic CD4$^+$ T cells (43, 50). It has been recently described that IL-10 inhibits endothelium-dependent T-cell activation by promoting ILT-4 expression on endothelial cells (52).

ILT-4 expressed on Tr-DC plays a role in the induction of Tr1 cells, since stimulation of naïve CD4$^+$ T cells with Tr-DC in the presence of neutralizing anti-ILT-4 mAb prevented the induction of anergic T cells (FIG. 10C) with suppressive activity (FIG. 10D, and FIG. 11A). Since ILT-4 binds to HLA-G, a non-classical HLA class I molecule (44), the authors next investigated the expression of HLA-G on CD4$^+$ T cells activated with Tr-DC. Freshly isolated naïve CD4$^+$ T cells express mean percentage of HLA-G of 2.2±0.9% (mean±SD, n=4) (data not shown) but after priming with Tr-DC the expression was up-regulated and T(Tr-DC) cell lines expressed significantly higher levels of HLA-G compared to T cells stimulated with iDC, and with mDC (FIG. 10E). In T-cell cultures stimulated with Tr-DC the percentage of CD4$^+$HLA-G$^+$ T cells was 17.7±6.7% versus 6.7±3.4% CD4$^+$HLA-G$^+$ T cells in cultures with iDC (n=7, p=0.001$^4$), and 11.1±7.7% CD4$^+$HLA-G$^+$ T cells in cultures with mDC (n=7, p=0.05). Importantly, the induction of HLA-G expression on T cells cultured with DC-10 was IL-10 dependent since priming of naïve CD4$^+$ T cells with Tr-DC in the presence of anti-IL-10R blocking mAb prevented HLA-G up-regulation (FIG. 10E). These results indicate that autocrine production of IL-10 by Tr-DC not only up-regulates ILT-4 and HLA-G on DC (data not shown), but it is also required for HLA-G up-regulation on CD4$^+$ T cells. The role of IL-10 in promoting HLA-G expression on APC has been previously shown (53), but this is the first demonstration that IL-10 up-regulates HLA-G expression also on CD4$^+$ T cells. To further prove that ILT-4/HLA-G interaction leads to Tr1 cell differentiation driven by Tr-DC, naïve CD4$^+$ T cells were stimulated with Tr-DC in the presence of neutralizing anti-HLA-G mAb. Activation of T cells with Tr-DC in the presence of neutralizing anti-HLA-G mAb prevented the induction of anergic T cells (FIG. 10F) with suppressive activity (FIG. 10G, and FIG. 11B). Taken together these results demonstrate that interaction between ILT-4 and IL-10-induced HLA-G is required for Tr1 cell differentiation. Moreover, these data also suggest that the indispensable role of IL-10 in Tr1 cell induction is due to its ability to up-regulate the tolerogenic molecules ILT-4 and HLA-G on both DC and T cells. HLA-G is a potent immuno-modulant, and is the major player in maintaining foetal-maternal tolerance (31). HLA-G inhibits cytolytic activity of NK and CTL (36), and allo-specific T-cell proliferation (38). Interestingly, a positive correlation between allograft acceptance and HLA-G expression on both graft cells (39, 40) and T cells (38) has been described, supporting a role of HLA-G in modulating allo-responses. Furthermore, it has been previously reported that HLA-G modulates DC function (54). Engagement of ILT-4 on DC by soluble HLA-G prevents the up-regulation of costimulatory molecules and inhibits their maturation (45), and DC treated with soluble HLA-G promote the induction of anergic/suppressor $CD4^+$ T cells (46). Here the authors demonstrate a key role of membrane-bound HLA-G in inducing human adaptive regulatory T cells.

In the present model system, IL-10 produced by tolerogenic Tr-DC inhibits T-cell proliferation and cytokine production, promotes T-cell anergy, up-regulates expression of ILT-4 on DC and modulates the expression of HLA-G on DC and T cells. ILT-4/HLA-G interaction enhances IL-10 production by Tr-DC amplifying this "tolerogenic" loop. Moreover, signals through HLA-G on T cells might contribute to T-cell anergy induction by inhibiting T-cell activation. It has been indeed recently proposed that HLA-G can act as signalling molecule (55). It cannot be excluded that additional pathways might synergize with the ILT-4/HLA-G interaction in promoting Tr1 cell differentiation. Tr-DC express ILT-2, the second ligand of HLA-G, and ILT-3, which might co-operate with ILT-4/HLA-G in inducing a tolerogenic response. Moreover, Tr-DC express HLA-G that might promote T-cell anergy by interacting with ILT-2 on T cells. It has been reported that ILT-2 engagement on T cells inhibits TCR-mediated signalling and prevents T-cell proliferation (56, 57).

Tr-DC Induce Anergic T Cells in Haplo-Identical and HLA-Matched Un-Related Pairs.

The authors next determine the ability of Tr-DC to induce T-cell anergy in pairs with different HLA disparities. Similarly to that observed using naïve $CD4^+$ T cells as responder cells, they demonstrated that Tr-DC elicited a lower proliferative response by allogeneic PBMC, with an average reduction of 89±10% (n=17, p<0.0005) and IFN-γ production with an average reduction of 95±10% (n=17, p<0.05), compared to that elicited by mature DC (FIG. 12). They then determined the ability of Tr-DC to induce anergic T cells. PBMC were co-cultured with Tr-DC at a 10:1 ratio for ten days as described in the Material and Methods, and subsequently tested for their ability to proliferate in response to the original allogeneic mature DC. PBMC primed with Tr-DC [T(Tr-DC)] were hypo-responsive to re-activation with the original allogeneic mature DC, whereas PBMC primed with mature DC [T(mDC)] were highly proliferative, as expected. An average reduction of 80±8% (n=18, p<0.0005) in Ag-induced proliferation of cells generated with Tr-DC was observed in comparison to PBMC primed with mature DC (FIG. 13).

The authors then determined the ability of Tr-DC to induce anergic T cells in haplo-identical and HLA-matched un-related (MUD) pairs. Results clearly demonstrated that Tr-DC induced anergic T cells in both settings. In FIG. 14 inhibition of secondary responses in haplo-identical pairs tested is shown. The mean value of anergy induced by Tr-DC was 78±8% (n=4, p=0.0007). Moreover, Tr-DC induced anergic T cells in MUD context with an average of 78±14% (n=3, p<0.0005) (FIG. 15). All together these results clearly indicate that cells generated with IL-10 are potent tolerogenic DC that induce anergic T cells, containing precursors or already differentiated Tr1 cells, to be used as cellular therapy to prevent/cure GvHD and organ graft rejection.

Comparison Between the Protocol to Anergize Cells with Exogenous IL-10 and with Tr-DC.

The ability to induce anergic T cells in haplo-identical pairs using Tr-DC was compared to that obtained using exogenous IL-10 and CD3-APC. PBMC were co-cultured with either Tr-DC or mDC at a 10:1 ratio or with CD3-depleted cells in the absence or presence of exogenous IL-10 at a ratio 1:1 for ten days, as described in the Material and Methods, and subsequently tested for their ability to proliferate in response to the original allogeneic mature DC. PBMC primed with both Tr-DC T(Tr-DC)] and CD3-depleted cells+IL-10 [T(MLR/IL-10)] were hypo-responsive to re-activation with mature DC. An average reduction of 78±8% (n=4), and of 67±33% (n=4) in Ag-induced proliferation of cells generated with Tr-DC and monocytes+IL-10 (MLR/IL-10) respectively, in comparison to PBMC primed with mature DC, was observed (FIG. 16). Importantly, while the protocol to anergize T cells with IL-10 fails to be successful in inducing high anergy in all of the donors, high anergy is obtained in T cell from all individuals tested with Tr-DC (Table II).

TABLE II

Tr-DC induce anergic T cells in all haplo-identical pairs.

| | 1 | 2 | 3 | 4 |
|---|---|---|---|---|
| | | ANERGY % | | |
| Tr1-DC | 79 | 79 | 68 | 88 |
| $CD3^-APC$ + IL-10 | 82 | 99 | 35 | 36 |

PBMC were stimulated with Tr-DC at 10:1 ratio or with CD3-depleted cells+IL-10 at 1:1 ratio for ten days. T-cell lines were tested for their ability to proliferate in response to mature allogeneic DC. Proliferative responses were evaluated by thymidine incorporation after 48 h of culture. Numbers represent the % of anergy compared to mDC. 1, 2, 3 and 4 represent different donors.

Generation of Tr-DC for Clinical Use.

To generate anergized T cells for clinical use the authors optimized the condition for the differentiation of Tr-DC. To this end they differentiated Tr-DC using medium containing either FCS or human serum (HS). The results obtained in eight different donors indicate that the phenotype of the differentiated Tr-DC in medium containing human serum is comparable to that obtained Tr-DC differentiated in medium containing FBS (FIG. 17A). Moreover, Tr-DC generated in medium containing FBS or HS are comparable in the ability to induce anergic T cells. An average reduction of 88±14% (n=2) and 78±8% (n=2) in Ag-induced proliferation of T cells primed with Tr-DC [T(Tr-DC)] differentiated in HS and in FBS cells, respectively, in comparison to T cells primed with mature DC [T(mDC)] was observed (FIG. 17B). Collectively, these data indicate that Tr-DC differentiated in medium containing HS are phenotypically identical to Tr-DC generated in medium containing FBS, and are equivalent in inducing anergic T cells.

Scale Up Procedure to Differentiate Tr-DC for Clinical Use.

To establish a procedure to generate Tr-DC for clinical use the authors differentiated Tr-DC in flask, and their phenotype and biological functions were compared to those of cells generated in plate. Tr-DC generated in flask and in plate are equivalent in term of phenotype and induce anergy in responder T cells in comparable manner. An average inhibition of 81±8% (n=4) and 78±4% (n=4) in Ag-induced proliferation of T cells primed with Tr-DC [T(Tr-DC)] generated in plate and in flask, respectively, in comparison to T cells primed with mature DC [T(mDC)], was observed (FIG. 18 and data not shown). These results indicate that Tr-DC generated in flask are comparable to that obtained in plate in inducing anergic T cells, and therefore suitable for clinical application according to the following scheme.

Scheme 1: Proposed cell therapy protocol.

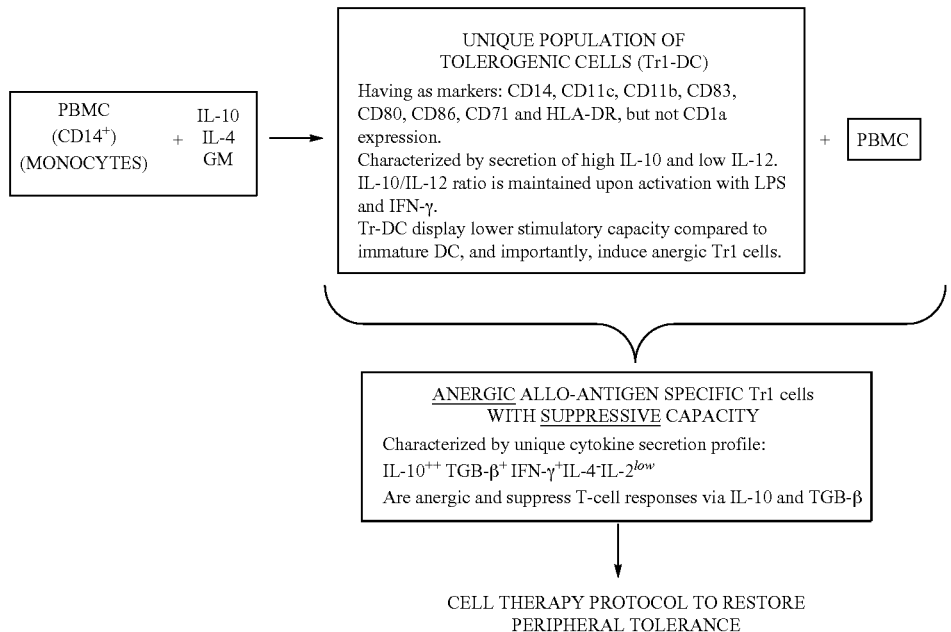

Anergic T cells can be injected by systemic route with a concentration ranging between $10^2$ to $10^8$ CD3+ cells/kg of body weight.

Tr-DC Also Exist In Vivo

It should be noted that Tr-DC (CD11c$^+$CD11b$^+$CD14$^+$ CD83$^+$CD1a$^-$) were identified in peripheral blood of normal donors where they represent 3.2±2.2% (mean±SD, n=6) of the mononuclear cells (FIG. 19A). To determine whether Tr-DC are present also in secondary lymphoid organs, the authors analyzed the spleen from normal donors. Interestingly, using CD14, CD11b, CD11c, CD83 and CD1a as markers, they demonstrated that Tr-DC cells are present in human spleen and represent 6.2±1.6% (mean±SD, n=4) of the total cells (FIG. 19B). Importantly, ILT-2, ILT-3, ILT-4, and HLA-G were also highly expressed on Tr-DC present in peripheral blood and spleen (FIGS. 20A and 20B). These findings show that Tr-DC are a distinct DC subset, which is not only inducible in vitro in the presence of exogenous IL-10, but also exist in vivo and thus can be directly isolated from the subject samples such as blood, spleen or lymph nodes.

Taken together these data indicate that Tr-DC, which are ILT3$^+$ILT4$^+$HLA-G$^+$IL-10$^{++}$IL-12$^{low/neg}$, represent a distinct subset of tolerogenic cells in vivo and can be differentiated in vitro with exogenous IL-10. Tr-DC produce high levels of IL-10 and are powerful inducers of Tr1 cells. Tr-DC drive Tr1 cell differentiation via the IL-10-dependent ILT-4/HLA-G pathway, since blocking of these tolerogenic molecules prevents Tr1 cell induction. Tr-DC set the stage for induction of regulatory T cells by secreting IL-10 that inhibits T-cell proliferation, up-regulates ILT-2, ILT-3, ILT-4, and HLA-G on DC, and induces HLA-G on T cells. The interaction between HLA-G and ILT-4 enhances IL-10 production by DC-10, which consequently may promote de novo expression of ILT-2, ILT-3, ILT-4, and HLA-G on other immature DC (FIG. 21). IL-10-induced HLA-G on DC and T cells represents a crucial component of the ILT-4 mediated mechanism of Tr1 cell differentiation. Thus, DC expressing ILT-4 and HLA-G and producing IL-10 are tolerogenic DC, which may be induced in vivo by antigens and pathogens as a way to escape immune responses. Overall our data demonstrate the central role of Tr-DC in the differentiation of adaptive Tr1 cells and identify ILT-4 and HLA-G as key surface molecules for tolerance induction.

Soluble HLA-G Induces Regulatory T Cells.

The authors next investigated the role of soluble HLA-G1 (sHLA-G) (Table III) in promoting regulatory T cells differentiation using a system of artificial APC consisting in murine L-cells co-transfected with hCD32, hCD80, and hCD58 (48).

TABLE III

Sequence of soluble HLA-G1

(SEQ ID No. 1)
MVVMAPRTLFLLLSGALTLTETWAGSHSMRYFSAAVSRPGRGEPRFIAMG

YVDDTQFVRFDSDSACPRMEPRAPWVEQEGPEYWEEETRNTKAHAQTDRM

NLQTLRGYYNQSEASSHTLQWMIGCDLGSDGRLLRGYEQYAYDGKDYLAL

NEDLRSWTAADTAAQISKRKCEAANVAEQRRAYLEGTCVEWLHRYLENGK

EMLQRADPPKTHVTHHPVFDYEATLRCWALGFYPAEIILTWQRDGEDQTQ

DVELVETRPAGDGTFQKWAAVVVPSGEEQRYTCHVQHEGLPEPLMLRWSK

EGDGGIMSVRESRSLSEDL

In this model repetitive stimulation of naïve human CD4$^+$ T cells in the presence of IL-10 and IFN-α polarized T cells into IL-10-producing Tr1 cells with low proliferative capacity and suppressor functions (47). The authors investigated whether IFN-α can be substituted by sHLA-G in this setting to promote Tr1 cell differentiation. Repetitive stimulation of naïve CD4$^+$ T cells with anti-CD3 cross-linked on CD32$^+$CD58$^+$CD80$^+$ L cells in the presence of sHLA-G alone (Tg) or in combination with IL-10 (Tg10) induce the differentiation of a population of CD4$^+$ T cells that produce TGF-β, intermediate levels of IL-10, low amounts of IFN-γ, but no IL-2, and IL-4 (FIGS. 22A and B). Tg cells obtained after two rounds of stimulation with anti-CD3 cross-linked on CD32$^+$CD58$^+$CD80$^+$ L cells in the presence of sHLA-G contained an intermediate proportion of IL-10-producing cells (average: 4%, range: 2-9%, n=5), and an intermediate proportion of IL-4-producing cells (average: 7%, range: 2-11%). In these culture conditions, IL-2-producing cells were on average 7% (range 4.2-9.9%), and IFN-γ-producing cells were on average 14% (range: 6-23%). Tg10 cells obtained after two rounds of stimulation with anti-CD3 cross-linked on CD32$^+$CD58$^+$CD80$^+$ L cells in the presence of sHLA-G and IL-10 contained an intermediate proportion of IL-10-producing cells (average: 5%, range: 2-9%, n=5), and an intermediate proportion of IL-4-producing cells (average: 7%, range: 3-11%). In these culture conditions, IL-2-producing cells were on average 6% (range 3-8%), and IFN-γ-producing cells were on average 12% (range: 4-22%). Conversely, T cells differentiated with anti-CD3 cross-linked on CD32$^+$CD58$^+$CD80$^+$ L cells in the presence of IL-10 and IFN-α (Tr1) contained a higher proportion of IL-10-producing cells (on average 12%, range: 5-16%, n=7), IFN-γ-producing cells (on average 31%, range: 18-42%, n=7), and IL-2-producing cells (on average 13%, range: 6-20%, n=7), but low IL-4-producing cells (on average 3%, range: 1.3-7%, n=7), (FIG. 23A). These results were paralleled with resulted obtained by measuring cytokine in culture supernatants (FIG. 22B).

Phenotypic analysis of Tg and Tg10 cell lines revealed a percentage of CD25$^+$FOXP3$^+$ cells similar to that observed in Tr1 cell lines (FIG. 23A). The percentage of Tg and Tg10 cells expressing CTLA-4 was higher compared to that observed in Tr1 cells (FIG. 23B). Interestingly, the percentage of T cells expressing HLA-G was comparable among the T cell lines (Tg, Tg10, and Tr1 cells), but higher compared to that of Th0 cells. Interestingly, the percentage of Tg, Tg10 and Tr1 cells expressing granzyme B was also higher compared to that observed in Th0 cells, whereas the percentage of cells expressing granzyme A was comparable among the Tg and Tg10 but lower compared to Tr1 cells (FIG. 23C). In summary, the T cells differentiated with anti-CD3 cross-linked on CD32$^+$CD58$^+$CD80$^+$ L cells in the presence of sHLA-G alone (Tg) or in combination with IL-10 (Tg10) are phenotypically similar to Tr1 cells but secrete lower amount of IL-10 and IFN-γ and do not secrete IL-2.

T cells differentiated with anti-CD3 cross-linked on CD32$^+$CD58$^+$CD80$^+$ L cells in the presence of sHLA-G alone (Tg) or in combination with IL-10 (Tg10) display low proliferative capacity (data not shown) and suppress primary T-cell responses. Proliferation of naïve CD4$^+$ T cells stimulated with coated anti-CD3 and soluble anti-CD28 mAbs was significantly suppressed by the addition of Tg and Tg10 cells (FIG. 24A).

In summary, the present invention indicates that:
i) IL-10 modulated DC (Tr-DC) are a novel subset of tolerogenic DC that are CD14$^+$CD11c$^+$CD11b$^+$CD83$^+$HLA-DR$^+$CD1a$^-$,
ii) IL-10 modulated DC (Tr-DC) are a novel subset of tolerogenic DC that display a mature myeloid phenotype (CD80$^+$CD86$^+$)
iii) IL-10 modulated DC (Tr-DC) are a novel subset of tolerogenic DC that express immunoglobulin-like transcript (ILT)-2, ILT-3, ILT-4, and HLA-G
iv) IL-10 modulated DC (Tr-DC) are a novel subset of tolerogenic DC that secrete high levels of IL-10 and low levels of IL-12, and are refractory to activation and maturation in vitro.
v) Tr-DC induce anergic T cells.
vi) Anergic T cells induced by Tr-DC are regulatory T cells phenotypically and functional similar to Tr1 cells.
vii) Tr-DC induce anergic T cells in pairs with different HLA disparities, which can be used as cellular therapy to prevent GvHD and organ allograft rejection.
viii) Soluble HLA-G1 alone or in combination with IL-10 promotes the differentiation of a population of CD4$^+$ T cells with suppressive activity.

In addition, anergized T cells generated with Tr-DC:
contain a significant proportion of Tr1 cells
are stable
are antigen-specific
are able to suppress Ag-specific primary responses
are induced by shot-term culture.

REFERENCES

1. Groux, H., A. O'Garra, M. Bigler, M. Rouleau, S. Antonenko, J. E. de Vries, and M. G. Roncarolo. 1997. A CD4+ T-cell subset inhibits antigen-specific T-cell responses and prevents colitis. *Nature* 389:737-742.
2. Shevach, E. M. 2002. CD4+ CD25+ suppressor T cells: more questions than answers. *Nat Rev Immunol* 2:389-400.
3. Moore, K. W., R. de Waal Malefyt, R. L. Coffman, and A. O'Garra. 2001. Interleukin-10 and the interleukin-10 receptor. *Annu Rev Immunol* 19:683-765.
4. Fiorentino, D. F., A. Zlotnik, P. Vieira, T. R. Mosmann, M. Howard, K. W. Moore, and A. O'Garra. 1991. IL-10 acts on the antigen-presenting cell to inhibit cytokine production by Th1 cells. *J Immunol* 146:3444-3451.
5. Willems, F., A. Marchant, J. P. Delville, C. Gerard, A. Delvaux, T. Velu, M. de Boer, and M. Goldman. 1994. Interleukin-10 inhibits B7 and intercellular adhesion molecule-1 expression on human monocytes. *Eur J Immunol* 24:1007-1009.
6. Fiorentino, D. F., A. Zlotnik, T. R. Mosmann, M. Howard, and A. O'Garra. 1991. IL-10 inhibits cytokine production by activated macrophages. *J Immunol* 147:3815-3822.
7. de Waal Malefyt, R., J. Haanen, H. Spits, M. G. Roncarolo, A. te Velde, C. Figdor, K. Johnson, R. Kastelein, H. Yssel, and J. E. de Vries. 1991. Interleukin 10 (IL-10) and viral IL-10 strongly reduce antigen-specific human T cell proliferation by diminishing the antigen-presenting capacity of monocytes via downregulation of class II major histocompatibility complex expression. *J Exp Med* 174:915-924.
8. Allavena, P., L. Piemonti, D. Longoni, S. Bernasconi, A. Stoppacciaro, L. Ruco, and A. Mantovani. 1998. IL-10 prevents the differentiation of monocytes to dendritic cells but promotes their maturation to macrophages. *Eur J Immunol* 28:359-369.
9. Groux, H., M. Bigler, J. E. de Vries, and M. G. Roncarolo. 1996. Interleukin-10 induces a long-term antigen-specific anergic state in human CD4+ T cells. *J Exp Med* 184:19-29.
10. Zeller, J. C., A. Panoskaltsis-Mortari, W. J. Murphy, F. W. Ruscetti, S. Narula, M. G. Roncarolo, and B. R. Blazar.

1999. Induction of CD4+ T cell alloantigen-specific hyporesponsiveness by IL-10 and TGF-beta. *J Immunol* 163:3684-3691.
11. Bacchetta, R., M. Bigler, J. L. Touraine, R. Parkman, P. A. Tovo, J. Abrams, R. de Waal Malefyt, J. E. de Vries, and M. G. Roncarolo. 1994. High levels of interleukin 10 production in vivo are associated with tolerance in SCID patients transplanted with HLA mismatched hematopoietic stem cells. *J Exp Med* 179:493-502.
12. Boussiotis, V. A., Z. M. Chen, J. C. Zeller, W. J. Murphy, A. Berezovskaya, S. Narula, M. G. Roncarolo, and B. R. Blazar. 2001. Altered T-cell receptor+CD28-mediated signaling and blocked cell cycle progression in interleukin 10 and transforming growth factor-beta-treated alloreactive T cells that do not induce graft-versus-host disease. *Blood* 97:565-571.
13. Banchereau, J., F. Briere, C. Caux, J. Davoust, S. Lebecque, Y. J. Liu, B. Pulendran, and K. Palucka. 2000. Immunobiology of dendritic cells. *Annu Rev Immunol* 18:767-811.
14. Roncarolo, M. G., M. K. Levings, and C. Traversari. 2001. Differentiation of T regulatory cells by immature dendritic cells. *J Exp Med* 193:F5-9.
15. Hawiger, D., K. Inaba, Y. Dorsett, M. Guo, K. Mahnke, M. Rivera, J. V. Ravetch, R. M. Steinman, and M. C. Nussenzweig. 2001. Dendritic cells induce peripheral T cell unresponsiveness under steady state conditions in vivo. *J Exp Med* 194:769-779.
16. Bonifaz, L., D. Bonnyay, K. Mahnke, M. Rivera, M. C. Nussenzweig, and R. M. Steinman. 2002. Efficient targeting of protein antigen to the dendritic cell receptor DEC-205 in the steady state leads to antigen presentation on major histocompatibility complex class I products and peripheral CD8+ T cell tolerance. *J Exp Med* 196:1627-1638.
17. Mahnke, K., Y. Qian, J. Knop, and A. H. Enk. 2003. Induction of CD4+/CD25+ regulatory T cells by targeting of antigens to immature dendritic cells. *Blood* 101:4862-4869.
18. Dhodapkar, M. V., R. M. Steinman, J. Krasovsky, C. Munz, and N. Bhardwaj. 2001. Antigen-specific inhibition of effector T cell function in humans after injection of immature dendritic cells. *J Exp Med* 193:233-238.
19. Jonuleit, H., E. Schmitt, G. Schuler, J. Knop, and A. H. Enk. 2000. Induction of interleukin 10-producing, nonproliferating CD4(+) T cells with regulatory properties by repetitive stimulation with allogeneic immature human dendritic cells. *J Exp Med* 192:1213-1222.
20. Levings, M. K., S. Gregori, E. Tresoldi, S. Cazzaniga, C. Bonini, and M. G. Roncarolo. 2005. Differentiation of Tr1 cells by immature dendritic cells requires IL-10 but not CD25+CD4+ Tr cells. *Blood* 105:1162-1169.
21. Sallusto, F., and A. Lanzavecchia. 1999. Mobilizing dendritic cells for tolerance, priming, and chronic inflammation. *J Exp Med* 189:611-614.
22. Woltman, A. M., and C. van Kooten. 2003. Functional modulation of dendritic cells to suppress adaptive immune responses. *J Leukoc Biol* 73:428-441.
23. Steinbrink, K., E. Graulich, S. Kubsch, J. Knop, and A. H. Enk. 2002. CD4(+) and CD8(+) anergic T cells induced by interleukin-10-treated human dendritic cells display antigen-specific suppressor activity. *Blood* 99:2468-2476.
24. Steinbrink, K., M. Wolfl, H. Jonuleit, J. Knop, and A. H. Enk. 1997. Induction of tolerance by IL-10-treated dendritic cells. *J Immunol* 159:4772-4780.
25. Sato, K., N. Yamashita, M. Baba, and T. Matsuyama. 2003. Modified myeloid dendritic cells act as regulatory dendritic cells to induce anergic and regulatory T cells. *Blood* 101:3581-3589.
26. Carbonneil, C., H. Saidi, V. Donkova-Petrini, and L. Weiss. 2004. Dendritic cells generated in the presence of interferon-alpha stimulate allogeneic CD4+ T-cell proliferation: modulation by autocrine IL-10, enhanced T-cell apoptosis and T regulatory type 1 cells. *Int Immunol* 16:1037-1052.
27. Ito, T., R. Amakawa, M. Inaba, S. Ikehara, K. Inaba, and S. Fukuhara. 2001. Differential regulation of human blood dendritic cell subsets by IFNs. *J Immunol* 166:2961-2969.
28. Menges, M., S. Rossner, C. Voigtlander, H. Schindler, N. A. Kukutsch, C. Bogdan, K. Erb, G. Schuler, and M. B. Lutz. 2002. Repetitive injections of dendritic cells matured with tumor necrosis factor alpha induce antigen-specific protection of mice from autoimmunity. *J Exp Med* 195:15-21.
29. Velten, F. W., K. Duperrier, J. Bohlender, P. Metharom, and S. Goerdt. 2004. A gene signature of inhibitory MHC receptors identifies a BDCA3(+) subset of IL-10-induced dendritic cells with reduced allostimulatory capacity in vitro. *Eur J Immunol* 34:2800-2811.
30. Buelens, C., V. Verhasselt, D. De Groote, K. Thielemans, M. Goldman, and F. Willems. 1997. Interleukin-10 prevents the generation of dendritic cells from human peripheral blood mononuclear cells cultured with interleukin-4 and granulocyte/macrophage-colony-stimulating factor. *Eur J Immunol* 27:756-762.
31. Hunt, J. S., M. G. Petroff, R. H. McIntire, and C. Ober. 2005. HLA-G and immune tolerance in pregnancy. *Faseb J* 19:681-693.
32. Park, B., S. Lee, E. Kim, S. Chang, M. Jin, and K. Ahn. 2001. The truncated cytoplasmic tail of HLA-G serves a quality-control function in post-ER compartments. *Immunity* 15:213-224.
33. Ishitani, A., and D. E. Geraghty. 1992. Alternative splicing of HLA-G transcripts yields proteins with primary structures resembling both class I and class II antigens. *Proc Natl Acad Sci USA* 89:3947-3951.
34. Fujii, T., A. Ishitani, and D. E. Geraghty. 1994. A soluble form of the HLA-G antigen is encoded by a messenger ribonucleic acid containing intron 4. *J Immunol* 153:5516-5524.
35. Rouas-Freiss, N., R. M. Goncalves, C. Menier, J. Dausset, and E. D. Carosella. 1997. Direct evidence to support the role of HLA-G in protecting the fetus from maternal uterine natural killer cytolysis. *Proc Natl Acad Sci USA* 94:11520-11525.
36. Riteau, B., N. Rouas-Freiss, C. Menier, P. Paul, J. Dausset, and E. D. Carosella. 2001. HLA-G2, -G3, and -G4 isoforms expressed as nonmature cell surface glycoproteins inhibit NK and antigen-specific CTL cytolysis. *J Immunol* 166:5018-5026.
37. Lila, N., N. Rouas-Freiss, J. Dausset, A. Carpentier, and E. D. Carosella. 2001. Soluble HLA-G protein secreted by allo-specific CD4+ T cells suppresses the allo-proliferative response: a CD4+ T cell regulatory mechanism. *Proc Natl Acad Sci USA* 98:12150-12155.
38. Le Rond, S., J. Le Maoult, C. Creput, C. Menier, M. Deschamps, G. Le Friec, L. Amiot, A. Durrbach, J. Dausset, E. D. Carosella, and N. Rouas-Freiss. 2004. Alloreactive CD4+ and CD8+ T cells express the immunotolerant HLA-G molecule in mixed lymphocyte reactions: in vivo implications in transplanted patients. *Eur J Immunol* 34:649-660.

39. Allan, D. S., M. Colonna, L. L. Lanier, T. D. Churakova, J. S. Abrams, S. A. Ellis, A. J. McMichael, and V. M. Braud. 1999. Tetrameric complexes of human histocompatibility leukocyte antigen (HLA)-G bind to peripheral blood myelomonocytic cells. *J Exp Med* 189:1149-1156.
40. Lila, N., A. Carpentier, C. Amrein, I. Khalil-Daher, J. Dausset, and E. D. Carosella. 2000. Implication of HLA-G molecule in heart-graft acceptance. *Lancet* 355:2138.
41. Rouas-Freiss, N., J. LeMaoult, P. Moreau, J. Dausset, and E. D. Carosella. 2003. HLA-G in transplantation: a relevant molecule for inhibition of graft rejection? *Am J Transplant* 3:11-16.
42. Rouas-Freiss, N., P. Moreau, C. Menier, and E. D. Carosella. 2003. HLA-G in cancer: a way to turn off the immune system. *Semin Cancer Biol* 13:325-336.
43. LeMaoult, J., I. Krawice-Radanne, J. Dausset, and E. D. Carosella. 2004. HLA-G1-expressing antigen-presenting cells induce immunosuppressive CD4+ T cells. *Proc Natl Acad Sci USA* 101:7064-7069.
44. Colonna, M., J. Samaridis, M. Cella, L. Angman, R. L. Allen, C. A. O'Callaghan, R. Dunbar, G. S. Ogg, V. Cerundolo, and A. Rolink. 1998. Human myelomonocytic cells express an inhibitory receptor for classical and nonclassical MHC class I molecules. *J Immunol* 160:3096-3100.
45. Liang, S., and A. Horuzsko. 2003. Mobilizing dendritic cells for tolerance by engagement of immune inhibitory receptors for HLA-G. *Hum Immunol* 64:1025-1032.
46. Ristich, V., S. Liang, W. Zhang, J. Wu, and A. Horuzsko. 2005. Tolerization of dendritic cells by HLA-G. *Eur J Immunol* 35:1133-1142.
47. Levings, M. K., R. Sangregorio, F. Galbiati, S. Squadrone, R. de Waal Malefyt, and M. G. Roncarolo. 2001. IFN-alpha and IL-10 induce the differentiation of human type 1 T regulatory cells. *J Immunol* 166:5530-5539.
48. de Waal Malefyt, R., S. Verma, M. T. Bejarano, M. Ranes-Goldberg, M. Hill, and H. Spits. 1993. CD2/LFA-3 or LFA-1/ICAM-1 but not CD28/B7 interactions can augment cytotoxicity by virus-specific CD8+ cytotoxic T lymphocytes. *Eur J Immunol* 23:418-424.
49. Barrat, F. J., D. J. Cua, A. Boonstra, D. F. Richards, C. Crain, H. F. Savelkoul, R. de Waal-Malefyt, R. L. Coffman, C. M. Hawrylowicz, and A. O'Garra. 2002. In vitro generation of interleukin 10-producing regulatory CD4(+) T cells is induced by immunosuppressive drugs and inhibited by T helper type 1 (Th1)- and Th2-inducing cytokines. *J Exp Med* 195:603-616.
50. Manavalan, J. S., P. C. Rossi, G. Vlad, F. Piazza, A. Yarilina, R. Cortesini, D. Mancini, and N. Suciu-Foca. 2003. High expression of ILT3 and ILT4 is a general feature of tolerogenic dendritic cells. *Transpl Immunol* 11:245-258.
51. Penna, G., A. Roncari, S. Amuchastegui, K. C. Daniel, E. Berti, M. Colonna, and L. Adorini. 2005. Expression of the inhibitory receptor ILT3 on dendritic cells is dispensable for induction of CD4+Foxp3+ regulatory T cells by 1,25-dihydroxyvitamin D3. *Blood* 106:3490-3497.
52. Gleissner, C. A., A. Zastrow, R. Klingenberg, M. S. Kluger, M. Konstandin, S. Celik, S. Haemmerling, V. Shankar, T. Giese, H. A. Katus, and T. J. Dengler. 2007. IL-10 inhibits endothelium-dependent T cell costimulation by up-regulation of ILT3/4 in human vascular endothelial cells. *Eur J Immunol* 37:177-192.
53. Moreau, P., F. Adrian-Cabestre, C. Menier, V. Guiard, L. Gourand, J. Dausset, E. D. Carosella, and P. Paul. 1999. IL-10 selectively induces HLA-G expression in human trophoblasts and monocytes. *Int Immunol* 11:803-811.
54. Le Friec, G., F. Gros, Y. Sebti, V. Guilloux, C. Pangault, R. Fauchet, and L. Amiot. 2004. Capacity of myeloid and plasmacytoid dendritic cells especially at mature stage to express and secrete HLA-G molecules. *J Leukoc Biol* 76:1125-1133.
55. Comiskey, M., K. E. Domino, and C. M. Warner. 2007. HLA-G Is Found in Lipid Rafts and Can Act as a Signaling Molecule. *Hum Immunol* 68:1-11.
56. Saverino, D., M. Fabbi, F. Ghiotto, A. Merlo, S. Bruno, D. Zarcone, C. Tenca, M. Tiso, G. Santoro, G. Anastasi, D. Cosman, C. E. Grossi, and E. Ciccone. 2000. The CD85/LIR-1/ILT2 inhibitory receptor is expressed by all human T lymphocytes and down-regulates their functions. *J Immunol* 165:3742-3755.
57. Merlo, A., D. Saverino, C. Tenca, C. E. Grossi, S. Bruno, and E. Ciccone. 2001. CD85/LIR-1/ILT2 and CD152 (cytotoxic T lymphocyte antigen 4) inhibitory molecules down-regulate the cytolytic activity of human CD4+ T-cell clones specific for Mycobacterium tuberculosis. *Infect Immun* 69:6022-6029.

The invention claimed is:

1. An in vitro method for generating a population of human tolerogenic dendritic cells (Tr-DC) comprising the steps of:
   a) collecting peripheral blood mononuclear cells (PBMCs) from a subject;
   b) isolating adherent cells from collected PBMCs; and
   c) exposing said isolated adherent cells at the start of culture on day 0 to an effective amount of GM-CSF, IL-4 and IL-10 to generate human Tr-DC,
wherein the generated human Tr-DC have a mature myeloid phenotype and have a marker phenotype comprising: $CD14^+$, $CD11c^+$, $CD11b^+$, $CD83^+$, $CD80^+$, $CD86^+$, $HLA-DR^+$, $CD71^+$ and $CD1a^-$; wherein at least about 92% of the generated human Tr-DC are $CD86^+$ positive.

2. The in vitro method according to claim 1 wherein said adherent cells are $CD14^+$ monocytes.

3. The in vitro method according to claim 1 wherein the steps of isolating adherent cells and exposing said isolated adherent cells are performed in the presence of fetal calf serum (FCS) or of human serum (HS).

4. The in vitro method according to claim 1 wherein the effective amount of GM-CSF is between 1-1000 ng/ml.

5. The in vitro method according to claim 1 wherein the effective amount of IL-4 is between 1-1000 ng/ml.

6. The in vitro method according to claim 1 wherein the effective amount of IL-10 is between 1-1000 ng/ml.

7. The in vitro method of claim 1, wherein the marker phenotype of the generated population of human tolerogenic Tr-DC further comprises: $ILT-2^+$ and/or $ILT-3^+$ and/or $ILT-4^+$ and/or $HLA-G^+$.

8. The in vitro method of claim 1, wherein the generated population of human tolerogenic Tr-DC are capable of stimulating naive allogeneic $CD4^+$ T cells, wherein the stimulated allogeneic $CD4^+$ T cells, when activated, become Tr1 cells.

9. An in vitro method for generating a population of human tolerogenic dendritic cells (Tr-DC) comprising the steps of:
   a) collecting peripheral blood mononuclear cells (PBMCs) from a subject;
   b) isolating $CD14^+$ cells from collected PBMCs; and
   c) exposing said isolated $CD14^+$ cells at the start of culture on day 0 to an effective amount of GM-CSF, IL-4 and IL-10 to generate human Tr-DC,
wherein the generated human Tr-DC have a marker phenotype comprising: $CD14^+$, $CD11c^+$, $CD11b^+$, $CD80^+$, and $CD1a^-$; and wherein at least about 92% of the generated human Tr-DC are $CD86^+$.

10. The in vitro method of claim 1 wherein the GM-CSF of step (c) is rhGM-CSF in a concentration of 100 ng/ml, the IL-4 of step (c) is rhIL-4 in a concentration of 10 ng/ml and the IL-10 of step (c) is rhIL-10 in a concentration of 10 ng/ml.

11. The in vitro method of claim 9 wherein the GM-CSF of step (c) is rhGM-CSF in a concentration of 100 ng/ml, the IL-4 of step (c) is rhIL-4 in a concentration of 10 ng/ml and the IL-10 of step (c) is rhIL-10 in a concentration of 10 ng/ml.

12. The in vitro method of claim 1 wherein the step of exposing said isolated adherent cells to an effective amount of GM-CSF, IL-4 and IL-10 is conducted for 7 days in the presence of DC medium.

13. The in vitro method of claim 9 wherein the step of exposing said isolated CD14$^+$ cells to an effective amount of GM-CSF, IL-4 and IL-10 is conducted for 7 days in the presence of DC medium.

14. The in vitro method of claim 12 wherein the DC medium comprises RPMI 1640 supplemented with 10% FCS or 5% human serum, 100 U/ml penicillin/streptomycin and 50 μM 2 mercaptoethanol.

15. The in vitro method of claim 13 wherein the DC medium comprises RPMI 1640 supplemented with 10% FCS or 5% human serum, 100 U/ml penicillin/streptomycin and 50 μM 2 mercaptoethanol.

* * * * *